United States Patent
La et al.

(10) Patent No.: US 9,439,856 B2
(45) Date of Patent: Sep. 13, 2016

(54) METHOD OF PREPARING COMPOSITION FOR DELIVERING AN ANIONIC DRUG

(71) Applicant: Samyang Biopharmaceuticals Corporation, Seoul (KR)

(72) Inventors: Muhn-Ho La, Daejeon (KR); Ji-Yeon Son, Daejeon (KR); Sang-Hoon Kim, Seoul (KR)

(73) Assignee: Samyang Biopharmaceuticals Corporation, Seoul (KR)

( * ) Notice: Subject to any disclaimer, the term of this patent is extended or adjusted under 35 U.S.C. 154(b) by 0 days.

(21) Appl. No.: 14/388,043

(22) PCT Filed: Apr. 3, 2013

(86) PCT No.: PCT/KR2013/002765
§ 371 (c)(1),
(2) Date: Sep. 25, 2014

(87) PCT Pub. No.: WO2013/151326
PCT Pub. Date: Oct. 10, 2013

(65) Prior Publication Data
US 2015/0328152 A1    Nov. 19, 2015

(30) Foreign Application Priority Data
Apr. 4, 2012 (KR) .................. 10-2012-0035087

(51) Int. Cl.
*A61K 31/7088* (2006.01)
*A61K 31/713* (2006.01)
(Continued)

(52) U.S. Cl.
CPC ......... *A61K 9/1075* (2013.01); *A61K 31/7088* (2013.01); *A61K 31/713* (2013.01); *A61K 47/34* (2013.01); *A61K 47/48046* (2013.01); *C12N 15/88* (2013.01)

(58) Field of Classification Search
CPC ........... A61K 31/7088; A61K 31/713; A61K 47/34; A61K 47/48046; A61K 9/1075; C12N 15/88
See application file for complete search history.

(56) References Cited

U.S. PATENT DOCUMENTS 5,744,335 A * 4/1998 Wolff ................. C12N 15/87
435/458
6,322,805 B1   11/2001 Kim et al.
(Continued)

FOREIGN PATENT DOCUMENTS

KR     10-0180334      3/1999
KR     2010-0076905 A  7/2010
(Continued)

OTHER PUBLICATIONS

Elbashir et al., "RNA Interference is Mediated by 21- and 22-nucleotide RNAs", Genes Dev. 15, 2001, pp. 188-200.
(Continued)

*Primary Examiner* — Ernst V Arnold
(74) *Attorney, Agent, or Firm* — Marshall, Gerstein & Borun LLP

(57) ABSTRACT

Disclosed is an effective method of preparing a composition for delivering an anionic drug, the composition comprising an anionic drug as an active ingredient, a cationic lipid, and an amphiphilic block copolymer, wherein the anionic drug forms a complex with the cationic lipid, and the anionic drug/cationic lipid complex is entrapped in a micelle structure formed by the amphiphilic block copolymer.

19 Claims, 5 Drawing Sheets

(51) Int. Cl.
  *C12N 15/88* (2006.01)
  *A61K 9/107* (2006.01)
  *A61K 47/48* (2006.01)
  *A61K 47/34* (2006.01)

(56) References Cited

U.S. PATENT DOCUMENTS

| | | |
|---|---|---|
| 6,458,382 B1 | 10/2002 | Herweijer et al. |
| 6,852,334 B1 | 2/2005 | Cullis et al. |
| 2003/0073640 A1 | 4/2003 | Beigelman et al. |
| 2005/0064595 A1 | 3/2005 | MacLachlan et al. |
| 2005/0260261 A1 | 11/2005 | Huang et al. |
| 2006/0240093 A1 | 10/2006 | MacLachlan et al. |
| 2008/0260850 A1 | 10/2008 | Yi et al. |
| 2011/0268772 A1 | 11/2011 | Kim et al. |

FOREIGN PATENT DOCUMENTS

| | | |
|---|---|---|
| KR | 2011-0077818 A | 7/2011 |
| WO | WO-2005/007196 A2 | 1/2005 |
| WO | WO-2010/074540 A2 | 7/2010 |
| WO | WO-2012/091523 A2 | 7/2012 |

OTHER PUBLICATIONS

Gary et al., "Polymer-based siRNA Delivery: Perspectives on the Fundamental and Phenomenological Distinctions from Polymer-based DNA Delivery", Journal of Controlled Release 121, 2007, pp. 64-73.

McManus et al., "Gene Silencing in Mammals by Small Interfering RNAs", Nature Reviews, Genetics vol. 3, Oct. 2002, pp. 737-747.

Svensson et al., "Assessing siRNA Pharmacodynamics in a Luciferase-Expressing Mouse", Mol Ther. 16(12), Dec. 2008, pp. 1995-2001.

De Paula et al., "Hydrophobization and Bioconjugation for Enhanced siRNA Delivery and Targeting", RNA 13, 2007, pp. 431-456.

International Search Report and Written Opinion in Application No. PCT/KR2013/002765 dated Jul. 26, 2013.

\* cited by examiner

METHOD OF PREPARING COMPOSITION FOR DELIVERING AN ANIONIC DRUG

This application is a U.S. national phase application under 35 U.S.C. §371 of International Application No. PCT/KR2013/002765, filed on Apr. 3, 2013, entitled "Method of Preparing Composition for Delivering an Anionic Drug," which claims the priority of Korean Patent Application No. 10-2012-0035087 filed Apr. 4, 2012, the entire respective disclosures of which are incorporated herein by reference.

TECHNICAL FIELD

The present invention relates to an effective method of preparing a composition for delivering an anionic drug, the composition comprising an anionic drug as an active ingredient, a cationic lipid, and an amphiphilic block copolymer, wherein the anionic drug forms a complex with the cationic lipid, and the anionic drug/cationic lipid complex is entrapped in a micelle structure formed by the amphiphilic block copolymer.

BACKGROUND ART

In order to perform treatments using anionic drugs, particularly nucleic acid materials, safe and efficient drug delivery technologies have been studied for a long time, and various delivery systems and techniques have been developed. Particularly, delivery technologies employing viral delivery systems based on an adenovirus or a retrovirus, and non-viral delivery systems based on cationic lipids or cationic polymers have been developed.

However, it has been known that the technologies employing the viral delivery systems have problems in commercialization, including the risk of non-specific immune responses and the complexity in the production processes. For this reason, a recent research trend is to overcome the shortcomings of viral delivery systems by means of using non-viral delivery systems based on cationic lipids or cationic polymers. Such non-viral delivery systems are less efficient than viral delivery systems, but have the advantages of being accompanied by fewer side effects in vivo and having lower production costs.

Many studies have been conducted on non-viral delivery systems used for delivery of nucleic acid materials, and most typical examples thereof include a complex of cationic lipid and nucleic acid (lipoplex) and a complex of a polycationic polymer and nucleic acid (polyplex). This cationic lipid or polycationic polymer has been much studied, because it forms a complex by electrostatic interactions with an anionic drug, thereby stabilizing the anionic drug and increasing the intracellular delivery of the anionic drug (De Paula D, Bentley M V, Mahato R I, Hydrophobization and bioconjugation for enhanced siRNA delivery and targeting, RNA 13 (2007) 431-56; Gary D J, Puri N, Won Y Y, Polymer-based siRNA delivery: Perspectives on the fundamental and phenomenological distinctions from polymer-based DNA delivery, J Control release 121 (2007) 64-73).

However, if the cationic lipids or polycationic polymers developed to date are used in an amount required to obtain sufficient effects, they may cause serious toxicity—although less than that caused by viral delivery systems—indicating that they are unsuitable for therapeutic applications. In addition, a lipid-nucleic acid complex for intracellular delivery of the nucleic acid is widely used in cell line experiments, but it does not form a stable structure in blood, and thus it cannot be used in vivo (see U.S. Pat. No. 6,458,382).

Another non-viral delivery system that is used for the intracellular delivery of a nucleic acid in vivo is nucleic acid-cationic liposome complex or a cationic liposome containing a nucleic acid. It comprises an amphiphilic lipid, a neutral lipid, a fusogenic lipid, or the like, and the nucleic acid is electrically bound to the liposome or is entrapped in the liposome (US2003-0073640, WO05/007196, and US2006-0240093). However, this liposome delivery system may be easily captured by the reticuloendothelial system (RES) and show side effects with significant toxicity, indicating that it is unsuitable for systemic use. Also, the nucleic acid delivery effects thereof are mostly limited to liver tissue.

In addition, a non-viral delivery system that has been most frequently studied together with the liposome delivery system is a delivery system comprising a polycationic polymer containing a multivalent cationic charge per molecule. In this delivery system, a polymer that is frequently used is polycationic polyethyleneimine (PEI) based polymer, which is electrostatically bound to a nucleic acid to form a nanoparticle consisting of a nucleic acid-polymer complex. However, it is known that such polycationic polymers stimulate cell death and this cytotoxicity increases as the molecular weight and the degree of branching of the polymer increase. Also, it is known that polycationic polymers with low molecular weight have low cytotoxicity, but they cannot effectively form a complex with a nucleic acid due to their low cationic density, and thus they do not achieve the sufficient intracellular delivery of the nucleic acid and do not greatly contribute to the stability of the nucleic acid.

Another type of nucleic acid delivery system includes a delivery system obtained by conjugating a lipid or a polymer directly to a nucleic acid and then forming a complex of the conjugate with a micelle or another polymer to form a nanoparticle. However, conjugating the lipid or the polymer directly to the nucleic acid has difficulty in terms of conjugation efficiency or quality control, and the efficiency of nucleic acid delivery of this delivery system has not yet been clearly verified.

Therefore, it is required to develop an anionic drug delivery system in which the amount of cationic polymer or cationic lipid used can be minimized to reduce cytotoxicity and which is stable in blood and body fluid and can be delivered into cells to exhibit sufficient effects.

Meanwhile, there have been various attempts to use amphiphilic block copolymer to solubilize a poorly water-soluble drug in the form of a polymeric micelle and to stabilize the drug in an aqueous solution, thereby providing a drug delivery system (Korean Registered Patent No. 0180334). This amphiphilic block copolymer can solubilize a hydrophobic poorly water-soluble drug by forming polymeric micelles, but hydrophilic drugs such as anionic nucleic acids cannot be entrapped in the polymeric micelles, and thus the amphiphilic block copolymer is not suitable for delivery of these anionic drugs including nucleic acids. Thus, in order to deliver an anionic drug in the form of a polymeric micelle, a process of neutralizing the charge of the anionic drug using a cationic material is required. This process is disclosed in International Patent Publication No. WO 2010/074540.

Meanwhile, many diseases are caused by an increased expression of disease-related genes that occurs due to various factors or by abnormal activity caused by mutation. siRNA (short interfering RNA) inhibits the expression of a specific gene in a sequence-specific manner at the post-transcriptional stage, and receives a great deal of attention as a therapeutic agent. Particularly, due to its high activity and precise genetic selectivity, siRNA is expected as a therapeutic agent that can substitute for existing antisense nucleotides or ribozymes. siRNA is a short double-stranded RNA molecule composed of 15-30 nucleotides and cleaves the mRNA of a gene having a nucleotide sequence complementary thereto to inhibit the expression of the gene (McManus and Sharp, Nature Rev. Genet. 3:737 (2002); Elbashir, et al., Genes Dev. 15:188 (2001)).

Despite such advantages, siRNA is known to be rapidly degraded by nucleases in the blood and to be rapidly excreted through the kidney. In addition, it is known that siRNA does not easily pass through the cell membrane because it is negatively charged. For this reason, in order to use siRNA as a therapeutic agent, it is required to develop a technology for preparing a system for delivering siRNA, which can stabilize siRNA in vivo, deliver siRNA into a target cell or a target organ efficiently and show no toxicity.

DISCLOSURE

Technical Problem

An embodiment of the present invention provides an effective method of preparing a composition for delivering an anionic drug, which comprises a micelle structure capable of effectively delivering the anionic drug in vivo.

Another embodiment of the present invention provides a method of preparing a micelle particle comprising a complex of anionic drug and a cationic lipid, where the complex is formed by the anionic drug and a cationic lipid via an electrostatic interaction, and entrapped non-covalently interior of the micelle.

Technical Solution

An embodiment of the present invention relates to a method of preparing a composition for delivering an anionic drug, which comprises an anionic drug as an active ingredient, a cationic lipid, and an amphiphilic block copolymer, wherein the anionic drug forms a complex with the cationic lipid, and the anionic drug/cationic lipid complex is entrapped in a micelle structure formed of the amphiphilic block copolymer. This composition for anionic drug delivery is intended to increase the blood or in vivo stability of the anionic drug and to avoid the unwanted uptake by the reticuloendothelial system, such that the anionic drug can be efficiently delivered into a tissue in which it exhibits its effect. The preparation method of the present invention is also useful in mass-production of the composition for anionic drug delivery.

The present invention provides a method of preparing a composition for delivering an anionic drug. The composition for anionic drug delivery may be a pharmaceutical composition for anionic drug delivery comprising an anionic drug, a cationic lipid, and an amphiphilic block copolymer, wherein the anionic drug forms a complex with the cationic lipid, and the anionic drug/cationic lipid complex is entrapped in a micelle structure formed by the amphiphilic block copolymer.

The preparation method may comprise the steps of:

(1) adding an aqueous solution of an anionic drug to a solution of a cationic lipid in an organic solvent to prepare an emulsion; and (2) adding an aqueous solvent or an aqueous solution of an amphiphilic block copolymer to the prepared emulsion in step (1) to prepare a polymeric micelle, provided that, when the aqueous solvent is added in step (2), the method further comprises either the steps of adding the amphiphilic block copolymer to the solution of the cationic lipid in the organic solvent used in step (1), and then, removing the organic solvent from the emulsion prepared in step (1), or the steps of removing the organic solvent from the emulsion prepared in step (1), adding thereto a solution of the amphiphilic block copolymer in an organic solvent, and then, removing the organic solvent therefrom, and when the aqueous solution of the amphiphilic block copolymer is added in step (2), the method further comprises, after step (1) or (2), the step of removing the organic solvent.

More specifically, the preparation method may comprise the steps of:

(1-i') dissolving a portion of an amphiphilic block copolymer in an organic solvent, placing the solution into a vessel and removing the organic solvent, to coat the inside of the vessel with the amphiphilic block copolymer, wherein step (1-i') is an optional step and carried out before or after the following step (1-i);

(1-i) adding an aqueous solution of an anionic drug to a solution of a cationic lipid in an organic solvent to prepare an emulsion;

(1-ii) removing the organic solvent from the emulsion prepared in step (1-i), provided that, when step (1-i') is carried out, step (1-ii) is carried out in the vessel obtained in step (1-i') whose inside was coated with the amphiphilic block copolymer;

(1-iii) dissolving an amphiphilic block copolymer in an organic solvent, adding the amphiphilic block copolymer solution to the resultant of step (1-ii), and removing the organic solvent, provided that, when step (1-i') is carried out, the amphiphilic block copolymer in step (1-iii) means the remaining portion of the amphiphilic block copolymer, which is the unused portion of the amphiphilic block copolymer in step (1-i'); and (1-iv) adding an aqueous solvent to the organic solvent-removed resultant of step (1-iii) to form a polymeric micelle.

Step (1-i'), in which the solution of the amphiphilic block copolymer in the organic solvent is placed in the vessel and the organic solvent is removed, is a step for coating the inside of the vessel with the amphiphilic block copolymer. Step (1-i') is designed to prevent the micelles from adsorbing onto the inside surface of the vessel. This step (1-i') may optionally be carried out in order to increase the yield of anionic drug. Step (1-i') may be carried out before step (1-iii) of removing the organic solvent, for example, before or after step (1-i), or before or after step (1-ii). The solvent that is used in step (1-i') may be, for example, at least one selected from the group consisting of, but not limited to, ethyl acetate, acetonitrile, methylene chloride, chloroform, dioxane, and the like.

The amount of amphiphilic block copolymer that is used in step (1-i') may be about 1-99 wt %, preferably about 1-50 wt %, and more preferably about 5-50 wt %, based on the total amount of the amphiphilic block copolymer used in steps (1-i') and (1-iii). If the amount of amphiphilic block copolymer used in step (1-i') is less than 1 wt %, it will be difficult to harvest the complex of the anionic drug, the cationic lipid, and the amphiphilic block copolymer in step (1-iv), resulting in decreasing the yield of anionic drug. On the other hand, if the amount of amphiphilic block copolymer used in step (1-i') is more than 99 wt %, the size of the resulting nanoparticles will excessively increase, resulting in the decreased yield of anionic drug after filtration. For these reasons, the amount of the amphiphilic block copolymer used in step (1-i') is preferably within the above-specified range.

In step (1-i'), the organic solvent may be additionally added so that the total volume of the organic solvent used in step (1-i') may be greater than the total volume of step (1-i). Specifically, the total volume of the organic solvent that is used in step (1-i') may be greater than the total volume of the resultant of step (1-i), and preferably 1.2-1.5 times greater than the total volume of the resultant of step (1-i). If the total volume of the organic solvent that is used in step (1-i') is one time or less than the total volume of the resultant of step (1-i), the yield of step (1-iv) will decrease. In all the above-described steps, removal of the organic solvent may be performed by evaporation, but is not limited thereto.

Step (1-i), in which the aqueous solution of the anionic drug is mixed with the solution of the cationic lipid in the organic solution (organic solvent solution of the cationic lipid) to prepare the emulsion, may be carried out using any mixing device which is generally used in the preparation of emulsions, for example, a sonicator, a vortex mixer or stirrer, and this likewise applies to all the processes of preparing emulsions described below.

The concentration of the anionic drug in the aqueous solution of the anionic drug may be 1 ng/ml to 1 kg/ml, and specifically 1 µg/ml to 1 g/ml, and the concentration of the cationic lipid in the solution of the cationic lipid in the organic solvent may be 1 pg/ml to 1 kg/ml, and specifically 1 ng/ml to 1 g/ml. The mixing ratio by volume between the aqueous solution of the drug and the organic solvent solution of the cationic lipid may be, but is not limited to, 1:1-50, preferably 1:2-1:20, and more preferably 1:3-1:10 (the volume of the aqueous solution: the volume of the organic solvent solution). The mixing ratio by volume between the aqueous solution and the organic solvent solution may be determined as a proper ratio to form an emulsion.

In step (1-ii), the emulsion prepared in step (1-i) is placed in the vessel whose inside can be coated with the amphiphilic block copolymer in step (1-i'), and the organic solvent is removed therefrom, to form a thin film comprising the anionic drug/cationic lipid complex. Herein, the inside surface of the vessel is coated with the amphiphilic block copolymer, thereby preventing the yield decrease which may be caused by the adsorption of anionic drug/cationic lipid complex onto the inside of the vessel.

As described above, the remaining portion of the amphiphilic block copolymer that is used in step (1-iii) means the unused portion of the amphiphilic block copolymer in optional step (1-i'). The amount of the remaining portion of the amphiphilic block copolymer that is used in step (1-iii) may be 1 to 99 wt %, preferably 50 to 99 wt %, and more preferably 50 to 95 wt %, based on the total amount of the amphiphilic block copolymer used in steps (1-i') and (1-iii). If the optional step (1-i') is omitted, the entire required amount of the amphiphilic block copolymer is used in step (1-iii).

The organic solvent that is used in step (1-iii) to dissolve the amphiphilic block copolymer may be, for example, at least one selected from the group consisting of, but not limited to, ethyl acetate, acetonitrile, methylene chloride, chloroform, dioxane, and the like, and may be the same as or different from the organic solvent used in step (1-i'). Also, the amount of organic solvent used in step (1-iii) may be in the range so as to make the concentration of the amphiphilic block copolymer dissolved in the organic solvent solution be 1 ng/ml to 1 kg/ml, specifically 1 µg/ml to 1 g/ml.

In step (1-iii), the solution of the amphiphilic block copolymer in the organic solvent is added to the resultant of step (1-ii), that is, the thin film comprising the anionic drug/cationic lipid complex, after which the organic solvent is removed, whereby the thin film of amphiphilic block copolymer can be formed on thin film comprising the anionic drug/cationic lipid complex.

In step (1-iv), the aqueous solvent is used to hydrate the organic solvent-removed mixture resulted from step (1-iii), thereby preparing micelles. The aqueous solvent may be at least one selected from the group consisting of, but not limited to, water (e.g., distilled water) and buffer solution. The amount of aqueous solvent added may be in the range so as to make the expected concentration of the anionic drug after adding the aqueous solvent to be 1 ng/ml to 1 kg/ml, and specifically 1 µg/ml to 1 g/ml.

In step (1-iv), the resultant of step (1-iii), from which the organic solvent was removed, that is, the mixture of the thin film comprising the anionic drug/cationic lipid complex and the thin film of the amphiphilic block copolymer, is hydrated, thereby obtaining micelles which comprises the anionic drug, the cationic lipid and the amphiphilic block copolymer and in which the anionic drug/cationic lipid complex is entrapped in a micelle structure formed by the amphiphilic block copolymer.

In another embodiment, the preparation method may comprise the steps of:

(2-i') dissolving a portion of an amphiphilic block copolymer in an organic solvent, placing the solution into a vessel and removing the organic solvent to coat the inside of the vessel with the amphiphilic block copolymer, wherein step (2-i') is an optional step and carried out before or after the following step (2-i);

(2-i) adding an aqueous solution of an anionic drug to a solution of a cationic lipid in an organic solvent to prepare an emulsion;

(2-ii) removing the solvent from the emulsion prepared in step (2-i), provided that, when step (2-i') is carried out, step (2-ii) is carried out in the vessel whose inside was coated with the amphiphilic block copolymer in step (2-i'); and (2-iii) dissolving an amphiphilic block copolymer in an aqueous solvent, mixing the solution with the resultant of step (2-ii) to form a polymeric micelle, provided that, when step (2-i') is carried out, the amphiphilic block copolymer in step (2-iii) means the remaining portion of the amphiphilic block copolymer, which is the unused portion of the amphiphilic block copolymer in step (2-i').

The details of steps (2-i') to (2-ii) can be referred to the steps (1-i') to (1-ii), and step (2-i') may optionally be carried out in order to increase the yield of anionic drug, like step (1-i'). Step (2-i') may be carried out before step of (2-iii) of removing the solvent, for example, before or after step (2-i), or before or after step (2-ii).

In step (2-iii), the aqueous solution that is used to dissolve the remaining portion of the amphiphilic block copolymer may be at least one selected from the group consisting of water (distilled water) and buffer solution, and the amount of aqueous solution added may be in the range so as to make the expected concentration of the anionic drug after adding the aqueous solution of the amphiphilic block copolymer to be 1 ng/ml to 1 kg/ml, and specifically 1 µg/ml to 1 g/ml.

In step (2-iii), the resultant of step (2-ii), from which the organic solvent was removed, that is, the thin film comprising the anionic drug/cationic lipid complex, is hydrated by the aqueous solution of amphiphilic block copolymer, thereby obtaining nanoparticles which comprise the anionic drug, the cationic lipid and the amphiphilic block copolymer and in which the anionic drug/cationic lipid complex is entrapped in a micelle structure formed of the amphiphilic block copolymer.

In another embodiment, the preparation method may comprise the steps of:

(3-i') dissolving a portion of an amphiphilic block copolymer in an organic solvent, placing the solution into a vessel and removing the organic solvent from the solution to coat the inside of the vessel with the amphiphilic block copolymer, wherein step (3-i') is an optional step;

(3-i) adding an aqueous solution of an anionic drug to a solution of a cationic lipid and an amphiphilic block copolymer in an organic solvent to prepare an emulsion, provided that, when step (3-i') is carried out, the amphiphilic block copolymer in step (3-i) means the remaining portion of the amphiphilic block copolymer, which is the unused portion of the amphiphilic block copolymer in step (3-i');

(3-ii) removing the solvent from the emulsion prepared in step (3-i), provided that, when step (3-i') is carried out, step (3-ii) is carried out in the vessel whose inside was coated with the amphiphilic block copolymer in step (3-i'); and (3-iii) adding an aqueous solvent to the solvent-removed resultant of step (3-ii), to form a polymeric micelle.

The details of steps (3-i'), (3-ii) and (3-iii) can be referred to the steps (1-i'), (1-ii) and (1-iii), and step (3-i') may optionally be carried out in order to increase the yield of the process, like step (1-i'). Step (3-i') may be carried out before step of (3-iii) of removing the solvent, for example, before or after step (3-i), or before or after step (3-ii).

Step (3-i) is the same as step (1-i), except that the solution of the cationic lipid and the amphiphilic block copolymer (or the remaining portion of the amphiphilic block copolymer, which is the unused portion of the amphiphilic block copolymer in step (3-i')) in the organic solvent is used to prepare the emulsion. Also, the concentration of the aqueous solution of the anionic drug which is used in step (3-i) is as described above for step (1-i).

In another embodiment, the preparation method may comprise the steps of:

(4-i) adding an aqueous solution of an anionic drug to a solution of a cationic lipid in an organic solvent to prepare an emulsion;

(4-ii) adding the emulsion of (4-i) to an aqueous solution of an amphiphilic block copolymer to prepare a double emulsion; and (4-iii) selectively removing the organic solvent from the double emulsion prepared in step (4-ii), thereby forming a polymeric micelle.

The details of the step (4-i) can be referred to the step (1-i), and the mixing ratio by volume between the aqueous solution of the anionic drug and the solution of the cationic lipid in the organic solvent (organic solvent solution) may be 1:1-1:50, preferably 1:2-1:20, and more preferably 1:3-1:10 (the volume of the aqueous solution: the volume of the organic solvent solution), but is not limited thereto.

In step (4-ii), the entire amount of the amphiphilic block copolymer is used, and the aqueous solution of the amphiphilic block copolymer means an aqueous solution in which the amphiphilic block copolymer is dissolved in water at a concentration of 1 ng/ml to 1 kg/ml, specifically 1 µg/ml to 1 g/ml. In step (4-ii), the kind of aqueous solvent is as described above, and the amount of aqueous solvent used may be 1 to 1,000 times by volume, and specifically 1 to 100 times by volume, based on the volume of the emulsion of step (4-i).

In another embodiment, the preparation method may comprise the steps of:

(5-i) adding an aqueous solution of an anionic drug to a solution of a cationic lipid and an amphiphilic block copolymer in an organic solvent to prepare an emulsion;

(5-ii) adding the emulsion of step (5-i) to an aqueous solvent to prepare a double emulsion; and (5-iii) selectively removing the organic solvent from the double emulsion of step (5-ii), to form a polymeric micelle.

The details of steps of (5-i), (5-ii), and (5-iii) can be referred to the steps of (4-i), (4-ii), and (4-iii). In step (5-i), the mixing ratio by volume between the aqueous solution of the anionic drug and the solution of the cationic lipid and the amphiphilic block copolymer in the organic solvent (organic solvent solution) may be 1:1-1:50, preferably 1:2-1:20, and more preferably 1:3-1:10 (the volume of the aqueous solution: the volume of the organic solvent solution), but is not limited thereto.

In step (5-ii), the kind of aqueous solvent is as described above, and the amount of aqueous solvent used may be 1 to 1,000 times by volume, and specifically 1 to 100 times by volume, based on the volume of the emulsion of step (5-i).

The above-described steps, removal of the organic solvent may be performed by any conventional method, including evaporation, fractional distillation, and the like. Particularly, steps (4-iii) and (5-iii) of selectively removing the organic solvent may be performed by any method such as fractional distillation and the like.

In one embodiment, the above method 4 or 5 may further comprise, before the step of removing the organic solvent (e.g., before or after step (4-i), before or after step (4-ii), before or after step (5-i), or before or after step (5-ii)), a step of dissolving a portion of the amphiphilic block copolymer in an organic solvent, placing the solution in a vessel and then removing the organic solvent from the solution, thereby coating the inside of the vessel with the amphiphilic block copolymer. In this case, the amount of the amphiphilic block copolymer used in steps (4-ii) or (5-i) is the remaining amount of the amphiphilic block copolymer, which is the unused portion of the amphiphilic block copolymer in the coating step, and step (4-iii) or (5-iii) is carried out in the coated vessel.

In the above methods 1 to 5, the amphiphilic block copolymer functions to entrap the anionic drug/cationic lipid complex in aqueous solution into the micelle structure. The amount of amphiphilic block copolymer required in all the steps for preparing the composition for anionic drug delivery according to the present invention may be such an amount that the ratio of the weight of the anionic drug/cationic lipid (a) relative to the weight of the anionic drug/cationic lipid/amphiphilic block copolymer (b), [a/b×100; (anionic drug weight+cationic lipid weight)/(anionic drug weight+cationic lipid weight+amphiphilic block copolymer weight)×100], is 0.001% to 100%, preferably 0.01 to 50%, and more preferably 0.1 to 10%. If the weight ratio is less than 0.001 wt %, the content of the anionic drug/cationic lipid complex will decrease, thus making it difficult to achieve the effective content of the anionic drug. On the other hand, if the weight ratio is more than 100 wt %, a micelle structure of the suitable size cannot be formed after taking into consideration the molecular weight of the amphiphilic block copolymer and the amount of the anionic drug/cationic lipid complex.

In the above methods 1 to 3, when step (1-i'), (2-i') or (3-i') of coating the inside of the vessel with a portion of the amphiphilic block copolymer is carried out, the amount of the portion of amphiphilic block copolymer used to coat the inside of the vessel is the amount taken as the ratio described in step (1-i') relative to the entire amount calculated from the ratio of the weight of the anionic drug/cationic lipid (a) relative to the weight of the amphiphilic block copolymer (b), (a/b), and the amount of the remaining portion of amphiphilic block copolymer used in step (1-iii), (2-iii) or (3-ii) is the amount remaining after subtracting the amount of the portion described in step (1-i') from the whole amount calculated from the a/b ratio. Also, when step (1-i'), (2-i') or (3-i') is not carried out, the amount of amphiphilic block copolymer used in step (1-iii), (2-iii) or (3-ii) is the entire amount calculated from the a/b ratio.

The advantages of the above methods are that, because the compositions prepared thereby are in the form of nanoparticles having a uniform average particle size of 10-400 nm, specifically 50-300 nm, the yield can be maintained even after conventional subsequent steps such as sterile filtration are performed, so that a high yield can be achieved.

Improvements in the preparation method which is provided according to the present invention will now be described in comparison with the technology disclosed in a patent application previously filed by the applicant. WO 2010/074540 was filed by the applicant and discloses a method of preparing a composition for delivering an anionic drug, the method comprising the steps of:

(a) dissolving an anionic drug and a cationic lipid in a water-miscible solvent or a mixed solvent of an aqueous solution and an organic solvent;

(b) separating the organic solvent layer formed in step (a);

(c) adding an amphiphilic block copolymer to the organic solvent layer of step (b) and removing the organic solvent therefrom; and (d) adding an aqueous solution to the mixture of step (c) from which the organic solvent was removed, thereby forming a micelle.

Another preparation method disclosed in the previous patent application comprises the steps of:

(a') dissolving an anionic drug, a cationic lipid and an amphiphilic block copolymer in a water-miscible solvent or a mixed solvent of an aqueous solution and an organic solvent;

(b') removing the solvent from step (a'); and (c') adding an aqueous solution to the mixture of step (b') from which the organic solvent was removed, thereby forming a micelle.

Also, the previous patent application discloses that the preparation may further comprise a step of sterilizing the nanoparticles thus prepared; the sterilization step is necessary in order to use the nanoparticles as pharmaceuticals.

However, the preparation method disclosed in the previous patent application has a shortcoming in that the yield of the anionic drug entrapped in the nanoparticles after preparation is low. In order to find the cause of the low yield, the yield of anionic drug in the nanoparticles prepared through steps (a') to (c') of the method disclosed in the previous patent application was compared between before and after passage through a sterile filter. As a result, it was found that there was a significant difference in yield between before and after the filtration. This can suggest that the size of the produced nanoparticles is not uniform, and thus large particles are filtered out during the filtration. In addition, nanoparticles were prepared according to steps (a) to (d) of the method disclosed in the previous patent application, and the yield of the nanoparticles was compared between before and after passage through the sterile filter. Likewise, in the case of the nanoparticles prepared using this method, it was found that there was a significant difference in yield between before and after the filtration.

In the process of mixing the hydrophilic anionic drug with the hydrophobic cationic lipid to form a complex of the anionic drug and the cationic lipid, a water-miscible solvent or a mixed solvent of an aqueous solution and an organic solvent is used. Herein, in order to prevent phase separation between the aqueous solution and the organic solvent, a low-molecular-weight alcohol such as methanol or ethanol is usually used.

Thus, the present inventors have attempted various methods to make the size of nanoparticles uniform during their preparation. As a result, it was found that, in comparison with the previous method utilizing a water-miscible organic solvent or a mixed solvent of an aqueous solution and an organic solvent, a method of making an emulsion using a sonicator, a vortex mixer, a stirrer or the like either in a process of mixing an aqueous solution of an anionic drug with a solution of a cationic lipid in an organic solvent or in a process of mixing an aqueous solution of an anionic drug with a solution of a cationic lipid and an amphiphilic block copolymer in an organic solvent allows the size of particles to be more uniform, such that the difference in yield between before and after the filtration can be reduced, thereby completing the present invention.

Also, in the previous method, the anionic drug/cationic lipid complex or the anionic drug/cationic lipid/amphiphilic block copolymer complex was adsorbed onto the surface of a round bottom flask (vessel) in the process of removing the organic solvent, and the adsorbed material was not sufficiently dissolved into the aqueous solution layer during the hydration process, resulting in a decrease in yield before passage through a filter. In an attempt to solve this problem, the present inventors coated a portion of an amphiphilic block copolymer onto the inner wall of a vessel in which an anionic drug and a cationic lipid would come into contact with each other, before removing a solvent from a mixture of the anionic drug and the cationic lipid, in order to reduce the degree of adsorption of the anionic drug/cationic lipid complex onto the vessel, and as a result, the present inventors found the effect of reducing the loss of yield before the filtration (corresponding to steps (1-i'), (2-i') and (3-i')).

In one embodiment, the method of preparing nanoparticles based on the anionic drug/cationic lipid complex and the amphiphilic block copolymer may comprise the steps of: adding an aqueous solution of the anionic drug to a solution of the cationic lipid in an organic solvent while making an emulsion using a conventional means such as a sonicator, a vortex mixer, a stirrer or the like; removing the solvent from the emulsion containing the anionic drug and the cationic lipid, thereby making a thin film comprising the anionic drug/cationic lipid complex; adding a solution of the amphiphilic block copolymer in an organic solvent to the thin film and removing the organic solvent therefrom, thereby making a thin film of the amphiphilic block copolymer thereon; and then adding an aqueous solvent to the thin film to hydrating the thin film (steps (1-i) to (1-iv)).

In another embodiment, the method of preparing nanoparticles based on the anionic drug/cationic lipid complex and the amphiphilic block copolymer may comprise the steps of: adding an aqueous solution of the anionic drug to a solution of the cationic lipid in an organic solvent while making an emulsion using a conventional means such as a sonicator, a vortex mixer, a stirrer or the like; removing the solvent from the emulsion containing the anionic drug and the cationic lipid, thereby making a thin film comprising the anionic drug/cationic lipid complex; and adding an aqueous solution containing the amphiphilic block copolymer to the thin film to hydrate the thin film (steps (2-i) to (2-iii)).

In still another embodiment, the method of preparing nanoparticles based on the anionic drug/cationic lipid complex and the amphiphilic block copolymer may comprise the steps of: adding an aqueous solution of the anionic drug to a solution of the cationic lipid and the amphiphilic block copolymer in an organic solvent while making an emulsion using a conventional means such as a sonicator, a vortex mixer, a stirrer or the like; removing the solvent from the emulsion containing the anionic drug, the cationic lipid and the amphiphilic block copolymer, thereby making a thin film comprising the anionic drug/cationic lipid/amphiphilic block copolymer complex; and adding an aqueous solvent to the thin film to hydrate the thin film (step (3-i) to (3-iii)).

Also, when the anionic drug/cationic lipid complex and the amphiphilic block copolymer are mixed with each other to prepare nanoparticles, the preparation may comprise, before the step of removing the solvent from the mixture of the anionic drug and the cationic lipid to make the thin film, a step of coating the inner wall of the vessel with a portion of the amphiphilic block copolymer, thereby reducing the degree of adsorption of the anionic drug/cationic lipid complex onto the vessel (corresponding to steps (1-i'), (2-i') and (3-i')).

In another embodiment, the method of preparing nanoparticles based on the anionic drug/cationic lipid complex and the amphiphilic block copolymer may comprise the steps of: adding an aqueous solution of the anionic drug to a solution of the cationic lipid in an organic solvent while making an emulsion using a conventional means such as a sonicator, a vortex mixer, a stirrer or the like; adding the emulsion to an aqueous solution containing the amphiphilic block copolymer, while making a double emulsion using a conventional mixing means such as a sonicator, a vortex mixer, a stirrer or the like; and removing the organic solvent from the double emulsion using a conventional method such as fractional distillation (steps (4-i) to (4-iii)).

In another embodiment, the method of preparing nanoparticles based on the anionic drug/cationic lipid complex and the amphiphilic block copolymer may comprise the steps of: adding an aqueous solution of the anionic drug to a solution of the cationic lipid and the amphiphilic block copolymer in an organic solvent while making an emulsion using a conventional means such as a sonicator, a vortex mixer, a stirrer or the like; adding the emulsion to an aqueous solvent while making a double emulsion using a conventional means such as a sonicator, a vortex mixer, a stirrer or the like; and removing the organic solvent from the double emulsion using a conventional method such as fractional distillation (steps (5-i) to (5-iii)).

The methods using the steps (4-i) to (4-iii) or the steps (5-i) to (5-iii) have an additional advantage in that the step of hydrating the thin film can be omitted, thereby the yield of anionic drug and the reproducibility of preparation efficiency are improved, because the portion of the complex adsorbed onto the inside wall of the vessel even after the hydration is the main cause of the loss of yield and it may be changed from batch to batch.

The methods using the steps (4-i) to (4-iii) or the steps (5-1) to (5-iii) have another additional advantages which come from the omission of thin film status. In order to dissolve the thin film comprising the anionic drug and the cationic lipid, a certain amount of amphiphilic block copolymer is necessary. However, since the methods using the steps (4-i) to (4-iii) or the steps (5-1) to (5-iii) have no step of dissolving the thin film, the micelle can be formed with lower amount of amphiphilic block copolymer compared with the methods involving the step of dissolving the thin film.

The present inventors have tested if the methods involving no step of dissolving the thin film can make the micelle structure comprising anionic drug, cationic lipid, and amphiphilic block copolymer with lower amount of amphiphilic block copolymer. As a result, it was found that, in comparison with the method involving the step of dissolving the thin film, the method involving no step of dissolving the thin film can make the micelle structure with about 1,000 times lower amount of amphiphilic block copolymer.

The composition for anionic drug delivery prepared by the preparation method of the present invention comprises: an anionic drug as an active ingredient; a cationic lipid; and a micelle structure comprising an amphiphilic block copolymer, wherein the anionic drug forms a complex with the cationic lipid, and the formed complex is entrapped in the micelle structure formed by the amphiphilic block copolymer.

Also, the composition for anionic drug delivery is characterized in that it is in the form of nanoparticles having a uniform average particle size of 10-400 nm, particularly 50-300 nm, so that the yield of the composition can be maintained even after subsequent steps such as sterile filtration are performed.

In one embodiment, the anionic drug is bound to the cationic lipid by electrostatic interaction to form a complex which is then entrapped in the micelle structure of the amphiphilic block copolymer. FIG. 1 shows the schematic structure of a polymeric micelle delivery system according to one embodiment of the present invention, in which a complex of an anionic drug and a cationic lipid is entrapped. Referring to FIG. 1, the anionic drug is bound to the cationic lipid by electrostatic interaction to form a complex of the anionic drug and the cationic lipid. The purpose of forming anionic drug/cationic lipid complex is to make hydrophilic anionic drug hydrophobic and to entrap it in the micelle structure formed by the amphiphilic block copolymer.

As shown in FIG. 1, in the micelle structure formed by the amphiphilic block copolymer, the hydrophilic moiety of the amphiphilic block copolymer forms the outer shell of the micelle structure in an aqueous environment, the hydrophobic moiety of the amphiphilic block copolymer forms the inner core, and the anionic drug/cationic lipid complex is entrapped in the hydrophobic core of the micelle structure.

The anionic drug/cationic lipid complex is entrapped in the polymeric micelle structure of the present invention, which increase the blood or in vivo stability of the complex. In one embodiment, the particle size of the micelles is 10-400 nm, and preferably 50-300 nm. The particle size range is an optimal range selected in view of the stability of the micelle structure, the contents of the components of the micelle structure, the absorption of the anionic drug in vivo, and the convenience of sterilization for providing a pharmaceutical composition.

The anionic drug according to one embodiment of the present invention is meant to include all pharmacologically active substances that have negative charges in physiological condition. In one embodiment, the anionic nature can be imparted from one or more functional groups selected from the group consisting of carboxyl, phosphate and sulfate groups, and functional groups bearing negative charges at a pH of 5 or more. In one embodiment, the anionic drug may be a peptide, a protein or a nucleic acid.

In another embodiment, the nucleic acid may be mainly consisting of such as deoxyribonucleic acid, ribonucleic acid, or a polynucleotide derivative wherein the backbone, sugar or base is chemically modified or the end of the nucleic acid is modified. More preferably, it may be one or more nucleic acids selected from the group consisting of RNA, DNA, siRNA (short interfering RNA), an aptamer, antisense oligodeoxynucleotide (ODN), antisense RNA, ribozyme and DNAzyme. Also, in order to increase the stability of the nucleic acid in blood or weaken the immune response, the backbone, sugar or base of the nucleic acid may be chemically modified or the end of the nucleic acid may be modified. Specifically, a portion of the phosphodiester bond of the nucleic acid may be substituted by a phosphorothioate or boranophosphate bond, or the nucleic acid may include at least one nucleotide wherein various functional groups such as a methyl group, a methoxyethyl group or fluorine are introduced in the 2'-OH position of some riboses.

In one embodiment, the cationic lipid is intended such that it is bound to the anionic drug by electrostatic interaction to form a complex which is then entrapped into the micelle structure of the amphiphilic block copolymer to form a nanoparticle. Thus, the cationic lipid may be any kind of lipid capable of forming a complex with the anionic drug by electrostatic interaction. Specifically, it may be a kind of lipid having at least one functional group, such as an amine group and the functional groups bearing positive charges at a pH of 10 or less.

For example, the cationic lipid may be at least one selected from the group consisting of N-(1-(2,3-dioleoyloxy)propyl-N,N,N-trimethylammonium chloride (DOTAP); N,N-dimethyl-(2,3-dioleoyloxy)propylamine (DODMA); N,N,N-trimethyl-(2,3-dioleoyloxy)propylamine (DOTMA), 3β-[N—(N',N',N'-trimetylaminoethane)carbomoyl]cholesterol (TC-cholesterol), 3β-[N—(N',N'-dimethylaminoethane)carbamoyl]cholesterol (DC-cholesterol), 3β-[N—(N'-monomethylaminoethane)carbamoyl]cholesterol (MC-cholesterol), 3β-[N-(aminoethane)carbamoyl]cholesterol (AC-cholesterol), cholesteroloxypropane-1-amine (COPA), N—(N'-aminoethane)carbamoylpropanoic tocopherol (AC-tocopherol) and N—(N'-methylaminoethane)carbamoylpropanoic tocopherol (MC-tocopherol), which have one functional group per molecule that can bear positive charges in an aqueous solution.

Alternatively, the cationic lipid may be a kind of lipid having a plurality of functional groups per molecule that can bear positive ions in an aqueous solution. Specifically, it may be at least one selected from the group consisting of N,N-dioleyl-N,N-dimethylammonium chloride (DODAC), N,N-distearyl-N,N-dimethylammonium bromide (DDAB), 1,2-diacyl-3-trimethylammonium-propane (TAP), and 1,2-diacyl-3-dimethylammonium-propane (DAP).

Also, the cationic lipid may include a cationic lipid in which a saturated or unsaturated hydrocarbon having 11 to 26 carbon atoms is bound to the amine functional group of 1-12 oligoethyleneamines, wherein the oligoethyleneamine may be represented by the following formula 1:

[Formula 1]

wherein n and m are each 0 to 12, with the proviso that 2 n+m 12, a and b are each 1 to 6, and R1 and R2 are each independently selected from saturated and unsaturated hydrocarbon groups having 11 to 25 carbon atoms.

In the definition of the oligoethyleneamine of formula 1, n and m may be independently 1 to 9, with the proviso that 2≤n+m≤10, and a and b may be an integer ranging from 2 to 4. For example, the oligoethyleneamine may be selected from the group consisting of diethylenetriamine, triethylenetetramine, tetraethylenepentamine, pentaethylenehexamine, hexaethyleneheptamine, heptaethyleneoctamine, octaethylenenonamine, nonaethylenedecamine, decaethyleneundecamine, undecaethylenedodecamine, dodecaethylenetridecamine and tridecaethylenetetradecamine.

The saturated or unsaturated hydrocarbon that is bound to the amine functional group is derived from fatty acids having 12 to 26 carbon atoms and may be at least one selected from the group consisting of lauroyl, myristoyl, palmitoyl, stearoyl, arachidoyl, behenoyl, lignoceroyl, cerotoyl, myristoleoyl, palmitoleoyl, Sapienoyl, oleoyl, linoleoyl, arachidonoyl, eicosapentaenoyl, erucoyl, and docosahexaenoyl.

In one embodiment, the amphiphilic block copolymer may be an A-B-type block copolymer comprising a hydrophilic A-block and a hydrophobic B-block. In an aqueous solution, the amphiphilic A-B-type block copolymer forms a core-shell type polymeric micelle, wherein the hydrophobic B-block forms a core (inner wall) and the hydrophilic A-block forms a shell (outer wall).

In one embodiment, the hydrophilic A-block may be at least one selected from the group consisting of polyalkyleneglycol, polyvinyl alcohol, polyvinyl pyrrolidone, polyacrylamide, and derivatives thereof. More preferably, the hydrophilic A-block may be at least one selected from the group consisting of monomethoxy polyethylene glycol, monoacetoxy polyethylene glycol, polyethylene glycol, a copolymer of polyethylene and propylene glycol, and polyvinyl pyrrolidone. In another embodiment, the number-average molecular weight of the hydrophilic A-block may be 200 to 50,000 Daltons, preferably 1,000 to 20,000 Daltons, and more preferably 1,000 to 5,000 Daltons.

The hydrophobic B-block may be a biocompatible and biodegradable polymer. In one embodiment, it may be at least one selected from the group consisting of polyester, polyanhydride, polyamino acid, polyorthoester, and polyphosphazine. More preferably, the hydrophobic B-block may be at least one selected from the group consisting of polylactide, polyglycolide, polycaprolactone, polydioxane-2-one, a copolymer of polylactide and glycolide, a copolymer of polylactide and polydioxane-2-one, a copolymer of polylactide and polycaprolactone, and a copolymer of polyglycolide and polycaprolactone. In another embodiment, the number-average molecular weight of the hydrophobic B-block may be 50 to 50,000 Daltons, preferably 200 to 20,000 Daltons, and more preferably 1,000 to 5,000 Daltons. Also, to increase hydrophobicity of the hydrophobic block to improve the stability of the micelle, tocopherol, cholesterol, or a saturated or unsaturated fatty acid having 10-36 carbon atoms may be chemically bound to the end of the hydrophobic B-block.

In another embodiment, with respect to the ratio between the contents of the hydrophilic block (A) and the hydrophobic block (B), the amphiphilic block copolymer may comprise 40-70 wt % of the hydrophilic block (A), and preferably 50-60 wt % of the hydrophilic block (A), based on the weight of the copolymer. For this reason, the content of the hydrophilic block (A) in the copolymer is preferably 40 wt % or more in order for the copolymer to have water solubility sufficient for forming micelles. If the content of the hydrophilic block (A) in the copolymer is less than 40 wt %, the solubility of the copolymer in water will be low, making it difficult to form a micelle from the copolymer; on the other hand, if the content is more than 70 wt %, the hydrophilicity of the copolymer will be too high and so the stability of the polymeric micelle will be low, and thus it will be difficult to solubilize a complex of the anionic drug and the cationic lipid. For this reason, the content of the hydrophilic block (A) in the copolymer is preferably 70 wt % or less in view of the stability of the micelle.

Advantageous Effects

The inventive method of preparing a pharmaceutical composition containing an anionic drug has advantages in that it can increase the content of the drug in the composition compared to the previous preparation method and can also increase the reproducibility of preparation of the composition.

MODE FOR INVENTION

Hereinafter, the present invention will be described in further detail with reference to examples. It is to be understood, however, that these examples are for illustrative purposes only and are not intended to limit the scope of the present invention.

Preparation Example 1

Synthesis of AC-cholesterol
(3β-[N-(aminoethane)carbamoyl]cholesterol)

For synthesis of AC-cholesterol, cholesteryl chloroformate (Sigma-Aldrich) and ethylenediamine (Sigma-Aldrich) were allowed to react with each other in the following manner.

1 g (2.23 mmol) of cholesteryl chloroformate was dissolved in 20 ml of chloroform, and in a separate reactor, a 20-fold equivalents of ethylenediamine was diluted with 30 ml of chloroform and kept at 4° C. The cholesteryl chloroformate solution was added slowly to the reactor containing ethylenediamine, and the mixture was allowed to react at room temperature for 3 hours. After completion of the reaction, the solvent was removed using a rotary evaporator (Buchi Labortechnik AG, R-2055), and the remaining material was dissolved in a small amount of chloroform, and then extracted with a saturated NaCl solution and NaCO3 to recover the chloroform layer.

Then, the solvent was removed using a rotary evaporator, and the remaining material was dissolved again in chloroform and separated by silica-gel chromatography. To the fraction eluted in the chloroform: methanol=9:1 (v/v), a hydrochloric acid solution was added in an amount of 50 equivalents relative to cholesteryl chloroformate, and methanol was added thereto in small amounts until a single phase was formed, thereby forming AC-cholesterol hydrochloride.

The solvent was completely removed by heating and distillation under reduced pressure with a rotary evaporator. The AC-cholesterol hydrochloride was dissolved in methanol at 60° C., and then cooled to 4° C., whereby it was re-crystallized. The yield was about 53%. Synthesis and purity of AC-cholesterol were analyzed by 1H-NMR. The purity was 99% or more.

Preparation Examples 2 to 4

Preparation of 1,6-dioleoyl triethylenetetramide, 1,5-dimyristoleoyl diethylenetriamide and 1,8-dilinoleoyl tetraethylenepentaamide 1,6-dioleoyl triethylenetetramide was synthesized in the following manner by a nucleophilic addition reaction between triethylenetetramine and oleoyl chloride.

1.12 g (7.5 mmol) of triethylenetetramine was added to 25 mL of dichloromethane and dissolved with stirring in an ice water bath at 5° C. for 30 minutes. To the solution, a solution of 2.00 g (6.0 mmol) of oleoyl chloride in 20 mL of dichloromethane in a separate reactor was added slowly dropwise while it was allowed to react at 5° C. for 3 hours. Due to hydrogen chloride produced during the reaction, unreacted triethylenetetramine HCl was precipitated. Before the end of the reaction, the upper layer solution was taken and analyzed by thin layer chromatography (TLC) with a mobile phase of ethanol:chloroform (2:1) to determine whether the reaction was completed.

Figure 1:
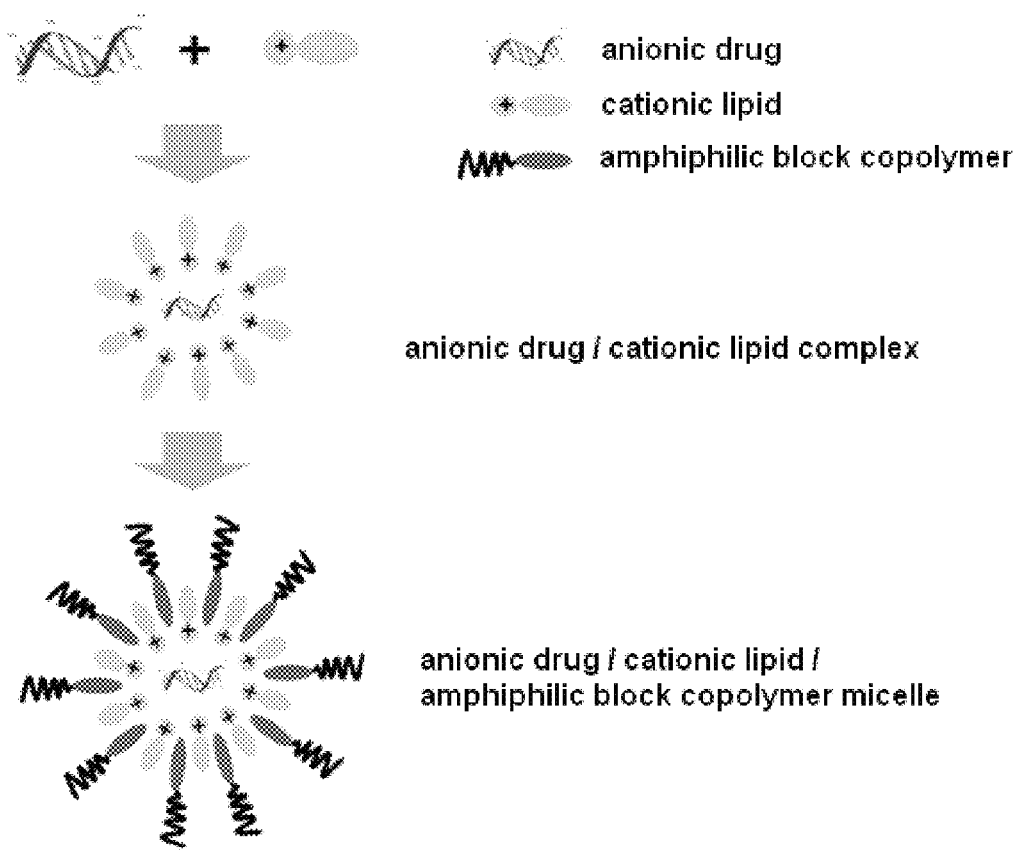
FIG. 1 is a schematic view of a composition for anionic drug delivery according to one embodiment of the present invention.
Figure 2:
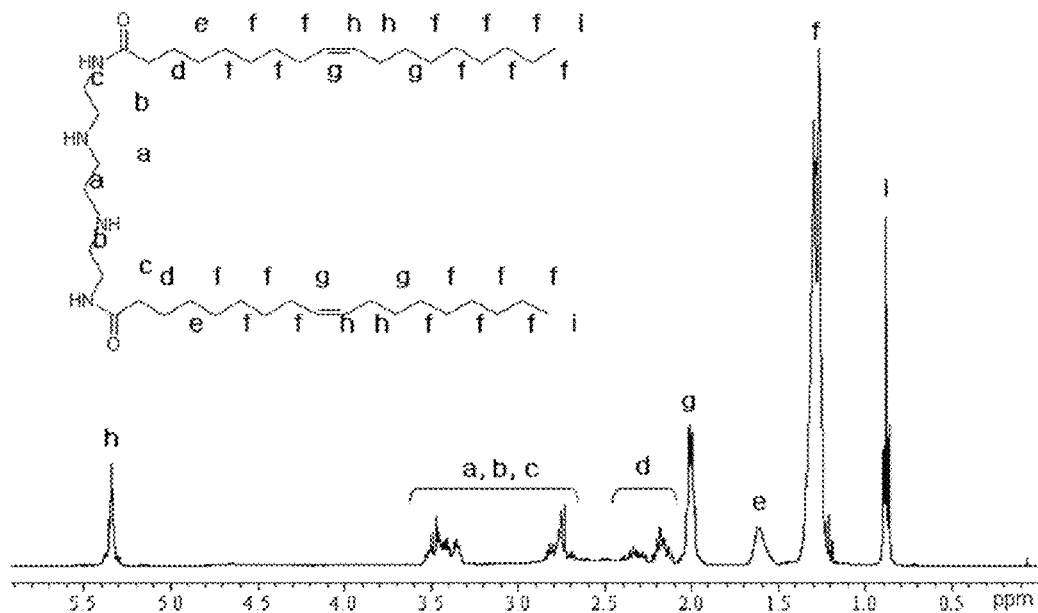
FIG. 2 shows the results of NMR measurement of 1,6-dioleoyl triethylenetetramide prepared by a preparation method according to one embodiment of the present invention.

After it was determined that the reaction had completed, the precipitate was removed using filter paper. Then, the filtered upper layer solution was evaporated in a rotary evaporator to remove the solvent and dried with a vacuum pump equipped with a cold trap. The resulting material was dissolved in 35 mL of diethyl ether and then extracted twice with 10 mL of 0.5 M NaOH in a separatory funnel. Then, the upper organic solvent layer was heated and distilled under reduced pressure in a rotary evaporator to completely remove the solvent, after which the remaining material was analyzed by thin layer chromatography to determine whether it was purified. The structure of the resulting product and the degree of introduction of an oleoyl group in the product were measured by a 1H NMR spectrometer. The obtained result is shown in FIG. 2. The yield of the product was 89.1%, and 2.1 equivalents of the oleoyl group was introduced in triethylenetetramine [Preparation Example 2].

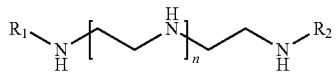

[Formula I]

wherein n is 2, and R1 and R2 are each hydrocarbons derived from unsaturated (C9) fatty acid having 18 carbon atoms.

Figure 3:
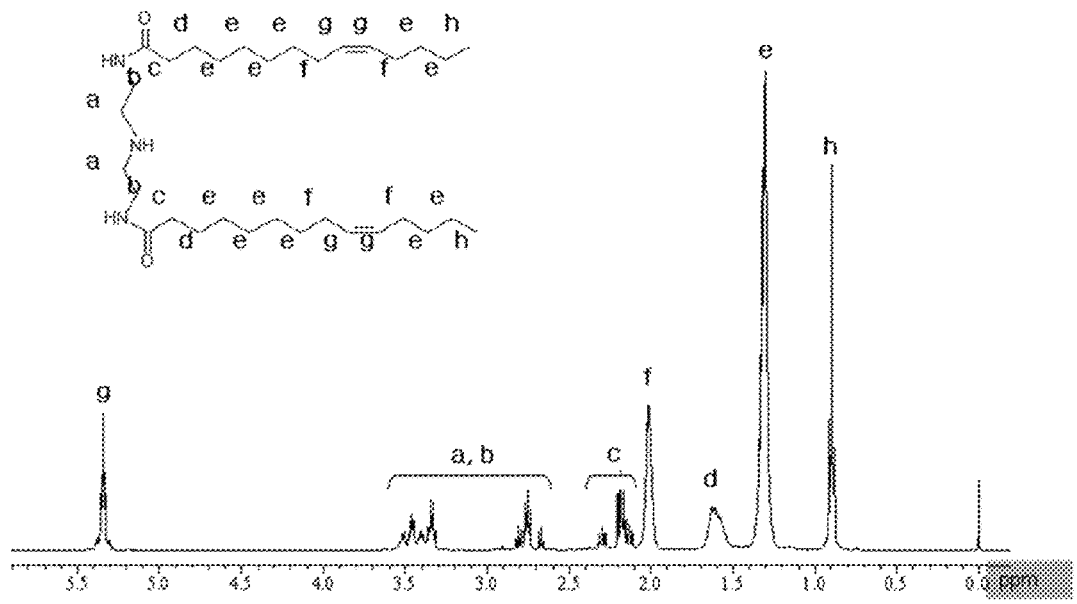
FIG. 3 shows the results of NMR measurement of 1,4-dimyristoleoyl diethylenetriamide prepared by a preparation method according to one embodiment of the present invention.
Figure 4:
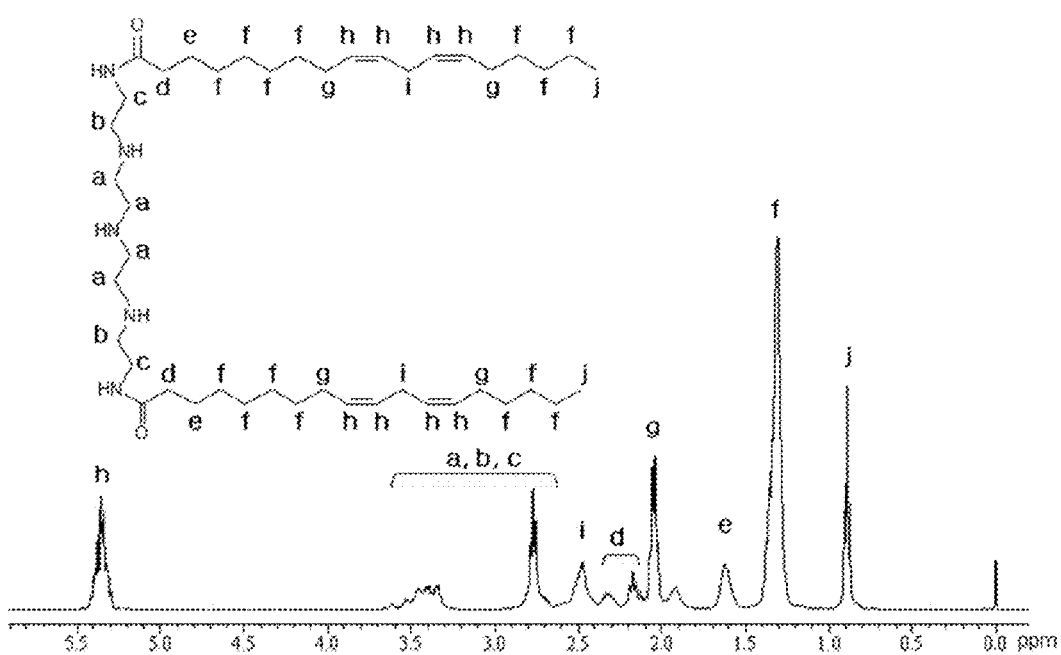
FIG. 4 shows the results of NMR measurement of 1,8-dilinoleoyl tetraethylenepentaamide prepared by a preparation method according to one embodiment of the present invention.

According to methods similar to the above method, 1,5-dimyristoleoyl diethylenetriamide [Preparation Example 3] and 1,8-dilinoleoyl tetraethylenepentaamide [Preparation Example 4] were synthesized. The 1H-NMR results of the obtained compounds are shown in FIGS. 3 and 4, respectively. Their yields were 40.5% and 28.0%, respectively, and the ratios of the lipids in the products were 2.24 equivalents and 1.82 equivalents, respectively.

Preparation Example 5

Synthesis of Monomethoxy Poly(Ethylene Glycol)-Lactide (mPEG-PLA) Block Copolymer (A-B) (Number-Average Molecular Weights: 5,000-4,000 Da)

10 g of monomethoxy poly(ethylene glycol) (molecular weight: 5,000 Da) was placed in a 100-mL 2-neck round bottom flask and dried in a vacuum (1 mmHg) at 120° C. for 5 hours. The reaction flask was charged with dry nitrogen, and a 50% solution of a stannous octoate (Sn(Oct)2) in toluene was injected into the flask together with 0.3 wt % (30 mg) of DL lactide with a syringe. The reaction mixture was stirred for 30 minutes and depressurized to 1 mmHg at 120° C. for 1 hour to remove toluene. 8.46 g of purified lactide was added thereto, and the mixture was heated at 130° C. for 6 hours. The mPEG-PLA obtained through the above process had number-average molecular weights of 5,000-4,000 Da and was determined to be an A-B type by 1H-NMR.

Preparation Example 6

Synthesis of mPEG-PLA-Tocopherol (Molecular Weights: 5,000-4,000-530 Da)

5 g of mPEG-PLA synthesized in Preparation Example 5 was placed in a 100-ml 2-neck round bottom flask and dried in a vacuum at 120° C. for 3 hours. A solution of 35.5 mg (645 μmol) of tocopherol acid succinylchloride in 3 mL of toluene was added thereto and allowed to react at 100° C. for 8 hours in a vacuum. The resulting polymer was dissolved in dichloromethane and precipitated in heptane, whereby it was purified. The purified polymer was dried in a vacuum to give white powder particles. The yield of the product was 94.2%, and as can be seen from the results of 1H-NMR analysis, the purity was 97.0% or more, and the rate of introduction of tocopherol was 99.9%.

Preparation Examples 7 to 11

Synthesis of mPEG-PLA-Pleate and mPEG-PLA-Linoleate

Figure 5:
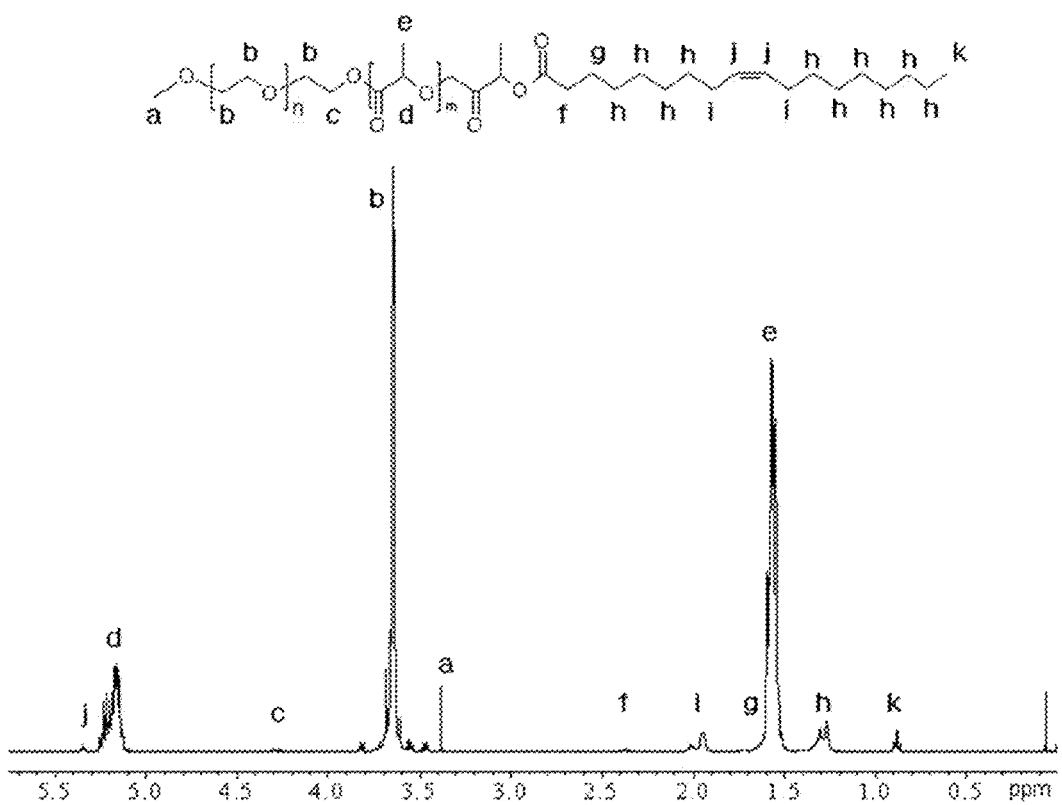
FIG. 5 shows the results of NMR measurement of a mPEG-PLA (5k-4k)-oleate prepared by a preparation method according to one embodiment of the present invention.
Figure 6:
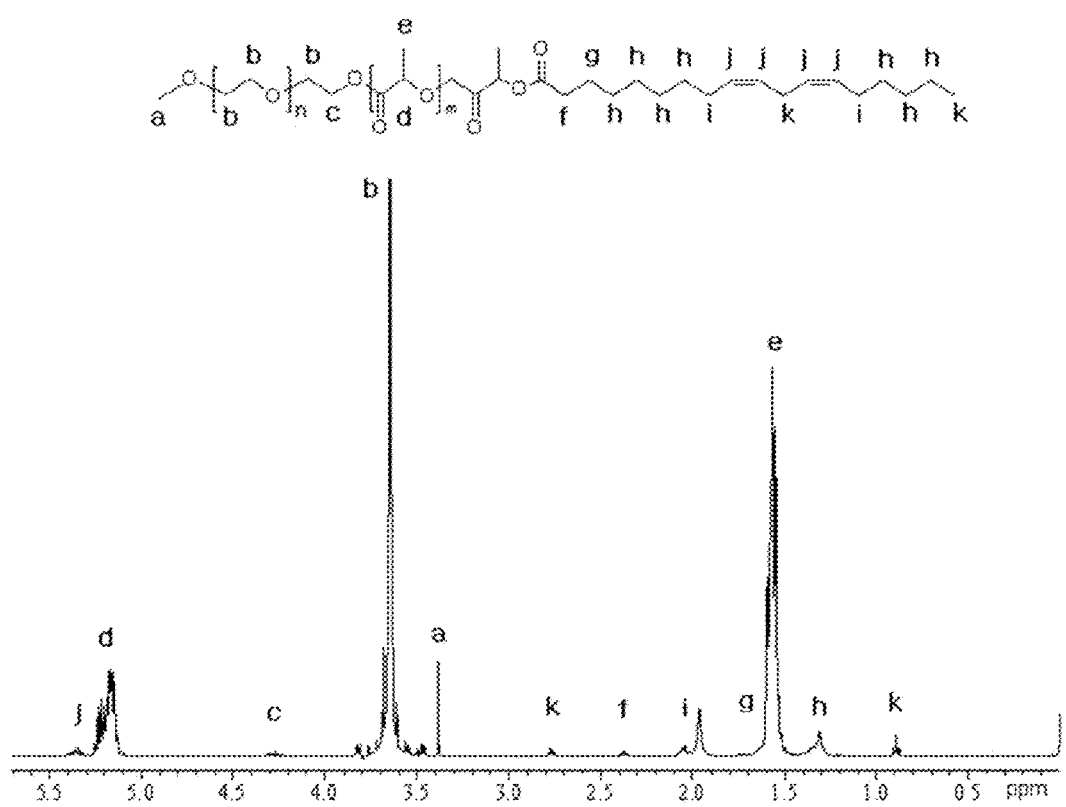
FIG. 6 shows the results of NMR measurement of a mPEG-PLA (5k-4k)-linoleate prepared by a preparation method according to one embodiment of the present invention.

According to the same method as Preparation Example 6, mPEG-PLA-oleate and mPEG-PLA-linoleate were synthesized to obtain the results shown in Table 1 below. The 1H-NMR results of the obtained compounds are shown in FIGS. 5 and 6, respectively.

TABLE 1

| Kind of polymer | Molecular weight (Da) | Yield (%) | Purity (%) | Rate of introduction of lipid |
|---|---|---|---|---|
| Preparation Example 7 | mPEG-PLA-tocopherol | 2,000-1,700-530 | 92.7 | 97 | 99.9 |
| Preparation Example 8 | mPEG-PLA-oleate | 5,000-4,000-265 | 64.0 | 99.7 | 99.9 |
| Preparation Example 9 | mPEG-PLA-oleate | 2,000-1,700-265 | 62.6 | 98.3 | 95.5 |
| Preparation Example 10 | mPEG-PLA-linoleate | 5,000-4,000-263 | 76.6 | 99.9 | 90.1 |
| Preparation Example 11 | mPEG-PLA-linoleate | 2,000-1,700-263 | 78.3 | 98.4 | 97.1 |

Comparative Example 1

Preparation of Composition Containing siRNA/AC-Cholesterol/mPEG-PLA-Tocopherol/DOPE (Preparation Method Using Water-Miscible Solvent)

345.0 ug of AC-cholesterol (N/P ratio: 9) prepared in Preparation Example 1 was dissolved in 17.3 ul of chloroform, and 25 ug of siRNA was dissolved in 20 ul of distilled water. 340.9 ug of DOPE was dissolved in 17.0 ul of chloroform and 15 mg of mPEG-PLA-tocopherol was dissolved in 0.5 ml of chloroform. The AC-cholesterol solution, the siRNA solution, the DOPE solution, and the mPEG-PLA-tocopherol solution were mixed with each other, so that the ratio of aqueous solution:chloroform:ethanol was adjusted to 1:1:2.

The siRNA used was an anti-luciferase siRNA, having 21 mer double strand (2 base overhang) structure (Mol. Ther. 16: 1995-2001 (2008)).

The mixture was placed in a one-neck round bottom flask and distilled under reduced pressure in a rotary evaporator to remove the solvent. 600 ul of distilled water was added to the flask which was then gently shaken to dissolve the residue, thereby preparing a composition (polymeric micelle) containing siRNA/AC-cholesterol/mPEG-PLA-tocopherol(5k-4k)/DOPE (see Table 2).

TABLE 2

| Composition | Composition ratio | siRNA | lipid | polymer |
|---|---|---|---|---|
| Comparative Example 1 | siRNA/AC-cholesterol/mPEG-PLA-tocopherol (5k-4k)/DOPE | 5-9-3 | 25 ug | 345 ug | 15 mg |

Example 1

Preparation of Composition Containing siRNA/AC-Cholesterol/mPEG-PLA-Tocopherol/DOPE (Removal of Solvent after Preparation of Emulsion)

345.0 ug of AC-cholesterol (N/P ratio: 9) prepared in Preparation Example 1 was dissolved in 17.3 ul of chloroform, and 25 ug of siRNA was dissolved in 20 ul of distilled water. 340.9 ug of DOPE was dissolved in 17.0 ul of chloroform and 15 mg of mPEG-PLA-tocopherol was dissolved in 0.5 ml of chloroform. The aqueous solution of siRNA was added dropwise to the chloroform solution containing AC-cholesterol, DOPE and mPEG-PLA-tocopherol while the mixture solution was sonicated using a sonicator, thus preparing an emulsion. The prepared emulsion was placed in a one-neck round bottom flask and distilled under reduced pressure in a rotary evaporator to remove the solvent. 600 ul of distilled water was added to the flask which was then gently shaken to residue the residue, thereby preparing a composition (polymeric micelle) containing siRNA/AC-cholesterol/mP EG-PLA-tocopherol(5k-4k)/DOPE.

Examples 2 and 3

Preparation of Composition Containing siRNA/AC-Cholesterol/mPEG-PLA-Tocopherol/DOPE (Removal of Solvent after Preparation of Emulsion)

345.0 ug of AC-cholesterol (N/P ratio: 9) prepared in Preparation Example 1 was dissolved in 17.3 ul of chloroform, and 25 ug of siRNA was dissolved in 20 ul of distilled water. 340.9 ug of DOPE was dissolved in 17.0 ul of chloroform and 15 mg of mPEG-PLA-tocopherol was dissolved in 0.5 ml of chloroform. Of the solution of 15 mg of mPEG-PLA-tocopherol in chloroform, 50 ul of the solution, which is a portion corresponding to 1.5 mg of mPEG-PLA-tocopherol (10 wt %), was placed in a one-neck round bottom flask, 600 ul of chloroform was added and mixed thereto, and then, distilled under reduced pressure in a rotary evaporator to remove the solvent. The remaining portion of the solution of mPEG-PLA-tocopherol (corresponding to 13.5 mg of mPEG-PLA-tocopherol) was mixed with the AC-cholesterol solution and the DOPE solution, and the aqueous solution of siRNA was added dropwise thereto while the mixture solution was sonicated using a sonicator, thus preparing an emulsion. The emulsion was placed in the one-neck round bottom flask to which 0.3 mg of mPEG-PLA-tocopherol was previously applied as described above, and it was distilled under reduced pressure in a rotary evaporator to remove the solvent. 600 ul of distilled water was added to the flask which was then gently shaken to dissolve the residue, thereby preparing a composition (polymeric micelle) containing siRNA/AC-cholesterol/mPEG-PLA-tocopherol(5k-4k)/DOPE (Example 2).

Example 3 was performed in the same manner as Example 2, except that, of the solution of 15 mg of mPEG-PLA-tocopherol, a portion corresponding to 0.3 mg of mPEG-PLA-tocopherol (2 wt %) was previously applied to the flask and that the remaining portion of the solution of mPEG-PLA-tocopherol (corresponding to 14.7 mg of mPEG-PLA-tocopherol) was mixed with AC-cholesterol and DOPE solutions.

The compositions obtained in Examples 1 to 3 are summarized in Table 3 below.

TABLE 3

| Compositions | | Composition ratio | siRNA | lipid | polymer |
|---|---|---|---|---|---|
| Examples 1 to 3 | siRNA/AC-cholesterol/mPEG-PLA-tocopherol (5k-4k)/DOPE | 5-9-3 | 25 ug | 345 ug | 15 mg |

Test Example 1

Comparison of siRNA Content Between Compositions Containing siRNA/AC-Cholesterol/mPEG-PLA-Tocopherol (5k-4k)/DOPE In order to examine the change in siRNA content according to the preparation method, the content of siRNA in each of the compositions prepared in Comparative Example 1 and Examples 1 to 3 was measured.

Using a modified Bligh & Dyer extraction method, siRNA in the prepared siRNA/cationic lipid-containing amphiphilic block copolymer micelles was quantified. Specifically, each of the polymeric micelles prepared in Comparative Example 1 and Examples 1 to 3 was dissolved in a solution of 50 mM sodium phosphate and 75 mM NaCl (pH 7.5), and a Bligh & Dyer single phase was made in the solution, after which the solution was extracted with 100 mM sodium phosphate, 150 mM NaCl (pH 7.5) and chloroform, and siRNA in the aqueous layer was quantified using Ribogreen reagent (Invitrogen).

As a sterile filter, Millipore 0.45 um PVDF filter was used. The results of the test are summarized in Table 4 below.

TABLE 4

| | Preparation method | Kind of polymer | Composition ratio | Content before filtration | Content after filtration |
|---|---|---|---|---|---|
| Comp. Example 1 | Use of water miscible solvent | siRNA/AC-cholesterol/mPEG-PLA-tocopherol (5k-4k)/DOPE | 5-9-3 | 99.8% | 42.4% |
| Example 1 | Removal of solvent after preparation of emulsion | siRNA/AC-cholesterol/mPEG-PLA-tocopherol (5k-4k)/DOPE | 5-9-3 | 38.3% | 34.7% |
| Example 2 | | siRNA/AC-cholesterol/mPEG-PLA-tocopherol (5k-4k)/DOPE | 5-9-3 | 85.8% | 63.0% |
| Example 3 | | siRNA/AC-cholesterol/mPEG-PLA-tocopherol (5k-4k)/DOPE | 5-9-3 | 63.8% | 49.9% |

As can be seen in Table 4 above, the loss of yield was significantly lower in the polymeric micelles, prepared according to the inventive method of removing the solvent after preparing the emulsion, than in the polymeric micelles prepared by the previous method utilizing the water miscible solvent. In addition, it was confirmed that the pretreatment process of coating the inside of the vessel had a significant effect on an increase in yield and a decrease in the loss of yield.

Comparative Example 2

Preparation of Composition Containing siRNA/1,6-Dioleoyl Triethylenetetramide (Dio-TETA)/mPEG-PLA-Oleate (5k-4k) (Composition Ratio: 5-15-6) (Use of Water Miscible Solvent)

3.43 mg of 1,6 dio-TETA was dissolved in 171.5 ul of chloroform, and 100 ug of siRNA was dissolved in 80 ul of distilled water. 120 mg of mPEG-PLA-oleate (5k-4k) was also dissolved in 400 ul of chloroform. The 1,6 dio-TETA solution and the siRNA solution were mixed together while the ratio of aqueous solution:chloroform:ethanol was adjusted to 1:1:2 (200 ul:200 ul:400 ul). To the obtained mixture, 200 ul of distilled water and 200 ul of chloroform were added to induce phase separation into an aqueous phase and an organic phase, and the organic phase was recovered and placed in a one-neck round bottom flask. The mPEG-PLA-oleate solution was added thereto and the content in the one-neck round bottom flask was distilled under reduced pressure in a rotary evaporator to remove the solvent. 2.4 ml of distilled water was added to the flask which was then gently shaken to dissolve the residue, thereby preparing a composition containing siRNA/1,6-dioTETA/mPEG-PLA-oleate (5k-4k) (see Table 5).

TABLE 5

| Composition | Composition ratio | siRNA | lipid | Polymer |
|---|---|---|---|---|
| Comparative Example 2 | siRNA/1,6-dioTETA/mPEG-PLA-oleate (5k-4k) | 5-15-6 | 100 ug | 3.43 mg | 120 mg |

Example 4

Preparation of Composition Containing siRNA/1,6-Dioleoyl Triethylenetetramide (Dio-TETA)/mPEG-PLA-Oleate (5k-4k) (Composition Ratio: 5-15-6) (Polymer-Containing Aqueous Solution and Double Emulsion after Preparation of Emulsion)

3.43 mg of 1,6 dio-TETA was dissolved in 400 ul of chloroform, and 100 ug of siRNA was dissolved in 80 ul of distilled water. 120 mg of mPEG-PLA-oleate (5k-4k) was dissolved in 2 ml of distilled water. The siRNA solution was added dropwise to the chloroform solution of 1,6 dio-TETA while the mixture solution was sonicated using a sonicator, thereby preparing an emulsion. The emulsion was added dropwise to the aqueous solution of mPEG-PLA-oleate while the mixture was sonicated using a sonicator, thereby preparing a double emulsion. The prepared double emulsion was placed in a one-neck round bottom flask and distilled under reduced pressure in a rotary evaporator to selectively remove the chloroform, thereby preparing a composition containing siRNA/1,6-dioleoyl triethylenetetramide (dio-TETA)/mPEG-PLA-oleate (5k-4k).

Example 5

Preparation of siRNA/1,6-Dioleoyl Triethylenetetramide (Dio-TETA)/mPEG-PLA-Oleate (5k-4k) (Composition Ratio: 5-15-6) (Aqueous Solution and Double Emulsion after Preparation of Emulsion)

3.43 mg of 1,6 dio-TETA was dissolved in 171.5 ul of chloroform, and 100 ug of siRNA was dissolved in 80 ul of distilled water. 120 mg of mPEG-PLA-oleate (5k-4k) was dissolved in 400 ul of chloroform. The siRNA solution was added dropwise to the chloroform solution of 1,6 dio-TETA and mPEG-PLA-oleate while the mixture solution was sonicated using a sonicator, thereby preparing an emulsion. The emulsion was added dropwise to 3 ml of distilled water while the solution was sonicated using a sonicator, thereby preparing a double emulsion. The prepared double emulsion was placed in a one-neck round bottom flask and distilled under reduced pressure in a rotary evaporator to selectively remove the chloroform, thereby preparing a composition containing siRNA/1,6-dioleoyl triethylenetetramide (dio-TETA)/mPEG-PLA-oleate (5k-4k) (see Table 6).

TABLE 6

| Compositions | | Composition ratio | siRNA | lipid | Polymer |
|---|---|---|---|---|---|
| Examples 4 and 5 | siRNA/1,6-dioTETA/mPEG-PLA-oleate (5k-4k) | 5-15-6 | 100 ug | 3.43 mg | 120 mg |

Test Example 2

Comparison of siRNA Content Between Compositions Containing siRNA/1,6-Dioleoyl Triethylenetetramide (dio-TETA)/mPEG-PLA-Oleate (5k-4k)

In order to examine the change in siRNA content according to the preparation method, the content of siRNA in each of the compositions prepared in Comparative Example 2 and Examples 4 and 5 was measured.

Using a modified Bligh & Dyer extraction method, siRNA in each of the siRNA/cationic lipid-containing amphiphilic block copolymer micelles prepared in Comparative Example 2 and Examples 4 and 5 was quantified. Specifically, each of the polymeric micelles was dissolved in a solution of 50 mM sodium phosphate and 75 mM NaCl (pH 7.5), and a Bligh & Dyer single phase was made in the solution, after which the solution was extracted with 100 mM sodium phosphate, 150 mM NaCl (pH 7.5) and chloroform, and siRNA in the aqueous layer was quantified using Ribogreen reagent (Invitrogen).

As a sterile filter, Millipore 0.45 um PVDF filter was used. The results of the test are shown in Table 7 below.

TABLE 7

| Preparation method | Kind of polymer | Composition ratio | Content before filtration | Content after filtration |
|---|---|---|---|---|
| Comp. Example 2 | Use of water miscible solvent | siRNA/dioTETA/mPEG-PLA-oleate (5k-4k) | 5-15-6 | 94.2% | 28.1% |
| Example 4 | Double emulsion after | siRNA/dioTETA/mPEG-PLA-oleate (5k-4k) | 5-15-6 | 72.8% | 70.1% |
| Example 5 | preparation of emulsion | siRNA/dioTETA/mPEG-PLA-oleate (5k-4k) | 5-15-6 | 80.9% | 73.8% |

As can be seen in Table 7 above, the loss of yield was significantly lower in the polymeric micelles, prepared according to the inventive method of removing the solvent after preparing the emulsion, than in the polymeric micelles prepared by the previous method utilizing the water miscible solvent.

Examples 6 and 7

Preparation of Composition Containing siRNA/dioTETA/mPEG-PLA-Tocopherol (2k-1.7k) (Preparation of Double Emulsion)

5.48 mg of dioTETA was dissolved in 274 ul of chloroform, and 200 ug of siRNA was dissolved in 160 ul of distilled water. 240 mg of mPEG-PLA-tocopherol (2k-1.7k) was dissolved in 1 ml of chloroform. Of the solution of 240 mg of mPEG-PLA-tocopherol in chloroform, 200 ul of the solution, which is a portion corresponding to 48 mg of mPEG-PLA-tocopherol (20 wt %), was placed in a one-neck round bottom flask, 1.3 ml of chloroform was added and mixed thereto, and then, distilled under reduced pressure in a rotary evaporator to remove the solvent.

Meanwhile, the dioTETA solution and the remaining portion of the solution of mPEG-PLA-tocopherol (corresponding to 192 mg mPEG-PLA-tocopherol) were mixed with each other, and the aqueous solution of siRNA was added thereto while the mixture solution was sonicated using a sonicator, thereby preparing an emulsion. The emulsion was added to 8 ml of distilled water while the solution was sonicated using a sonicator, thereby preparing a double emulsion. The double emulsion was placed in the one-neck round bottom flask to which 48 mg of mPEG-PLA-tocopherol was previously applied as described above, and the content in the flask was distilled under reduced pressure to remove chloroform, thereby preparing a composition containing siRNA/dioTETA/mPEG-PLA-tocopherol (2k-1.7k) (Example 6; see Table 8).

According to a method similar to the method of Example 6, a composition of Example 7 was prepared. Specifically, of the solution of 240 mg of mPEG-PLA-tocopherol, a portion corresponding to 120 mg of mPEG-PLA-tocopherol (50 wt %) was previously applied to the flask, and the remaining portion of the solution of mPEG-PLA-tocopherol (corresponding to 120 mg of mPEG-PLA-tocopherol) was mixed with dioTETA, thereby preparing a composition containing siRNA/dioTETA/mPEG-PLA-tocopherol (2k-1.7k) (Example 7; see Table 8).

Examples 8 and 9

Preparation of Composition Containing siRNA/dioTETA/mPEG-PLA-Linoleate (5k-4k) (Preparation of Double Emulsion)

6.86 mg of dioTETA was dissolved in 343 ul of chloroform, and 200 ug of siRNA was dissolved in 160 ul of distilled water. 120 mg of mPEG-PLA-linoleate (5k-4k) was dissolved in 1 ml of chloroform. Of the solution of 120 mg of mPEG-PLA-linoleate, a portion of the solution corresponding to 24 mg of mPEG-PLA-linoleate (20 wt %) was placed in a one-neck round bottom flask, 1.3 ml of chloroform was added and mixed thereto, and then, distilled under reduced in a rotary evaporator to remove the solvent. The dioTETA solution and the remaining portion of the solution of mPEG-PLA-linoleate (corresponding to 96 mg of mPEG-PLA-linoleate) were mixed with each other, and the aqueous solution of siRNA was added dropwise thereto while the mixture solution was sonicated using a sonicator, thereby preparing an emulsion. The emulsion was added dropwise to 8 ml of distilled water while the solution was sonicated using a sonicator, thereby preparing a double emulsion. The double emulsion was placed in the one-neck round bottom flask to which 24 mg of mPEG-PLA-linoleate was previously applied as described, and the content in the flask was distilled under reduced pressure in a rotary evaporator to remove chloroform, thereby preparing a composition containing siRNA/dioTETA/mPEG-PLA-linoleate (5k-4k) (Example 8; see Table 8).

According to a method similar to the method of Example 8, a composition of Example 9 was prepared. Specifically, of the solution of 120 mg of mPEG-PLA-linoleate, a portion corresponding to 60 mg of mPEG-PLA-linoleate (50 wt %) was previously applied to the flask, and the remaining portion of the solution of mPEG-PLA-linoleate (corresponding to 60 mg of mPEG-PLA-linoleate) was mixed with dioTETA, thereby preparing a composition containing siRNA/dioTETA/mPEG-PLA-linoleate (5k-4k) (Example 9; see Table 8).

TABLE 8

| Composition | Composition | Composition ratio | siRNA | lipid | Polymer |
|---|---|---|---|---|---|
| Examples 6 and 7 | siRNA/1,6-dioTETA/mPEG-PLA-tocopherol (2k-1.7k) | 5-12-6 | 200 ug | 5.48 mg | 240 mg |
| Examples 8 and 9 | siRNA/1,6-dioTETA/mPEG-PLA-linoleate (5k-4k) | 5-15-3 | 200 ug | 6.86 mg | 120 mg |

Test Example 3

Comparison of siRNA Content Between Compositions Containing siRNA/1,6-Dioleoyl Triethylenetetramide (dio-TETA)/mPEG-PLA-Tocopherol (2k-1.7k) or mPEG-PLA-Linoleate (5k-4k)

In order to examine the change in siRNA content according to the amount of the polymer used in pretreatment, the content of siRNA in each of the compositions prepared in Examples 6, 7, 8 and 9 was measured.

Using a modified Bligh & Dyer extraction method, siRNA in each of the siRNA/cationic lipid-containing amphiphilic block copolymer micelles prepared in Examples 6, 7, 8 and 9 was quantified. Specifically, each of the polymeric micelles was dissolved in a solution of 50 mM sodium phosphate and 75 mM NaCl (pH 7.5), and a Bligh & Dyer single phase was made in the solution, after which the solution was extracted with 100 mM sodium phosphate, 150 mM NaCl (pH 7.5) and chloroform, and siRNA in the aqueous layer was quantified using Ribogreen reagent (Invitrogen).

As a sterile filter, Millipore 0.45 um PVDF filter was used.

The results of the test are shown in Table 9 below.

TABLE 9

| | Preparation method (ratio of polymer used in pretreatment) | Kind of polymer | Composition ratio | Content before filtration | Content after filtration |
|---|---|---|---|---|---|
| Example 6 | 20% | siRNA/dioTETA/mPEG-PLA-tocopherol (2k-1.7k) | 5-12-6 | 75.6% | 63.2% |
| Example 7 | 50% | siRNA/dioTETA/mPEG-PLA-tocopherol (2k-1.7k) | 5-12-6 | 82.1% | 77.8% |
| Example 8 | 20% | siRNA/dioTETA/mPEG-PLA-linoleate (5k-4k) | 5-15-3 | 98.1% | 96.2% |
| Example 9 | 50% | siRNA/dioTETA/mPEG-PLA-linoleate (5k-4k) | 5-15-3 | 87.0% | 85.9% |

Example 10

Preparation of Composition Containing siRNA/1,4-Dimysteroyl Diethylenetriamine (dimyDETA)/mPEG-PLA-Tocopherol (5k-4k) (Removal of Solvent After Preparation of Emulsion)

830 ug of dimyDETA was dissolved in 41.5 ul of chloroform, and 25 ug of siRNA was dissolved in 20 ul of distilled water. 15 mg of mPEG-PLA-tocopherol (5k-4k) was also dissolved in 130 ul of chloroform. Of the solution of 15 mg of mPEG-PLA-tocopherol, a portion corresponding to 3 mg of mPEG-PLA-tocopherol (20 wt %) was placed in a one-neck round bottom flask, 1 ml of chloroform was added and mixed thereto, and then, distilled under reduced pressure in a rotary evaporator to remove the solvent. The dimyDETA solution and the remaining portion of the solution of mPEG-PLA-tocopherol corresponding to 12 mg of mPEG-PLA-tocopherol were mixed with each other, and the aqueous solution of siRNA was added dropwise thereto while the mixture solution was sonicated using a sonicator, thereby preparing an emulsion. The emulsion was placed in the one-neck round bottom flask to which 3 mg of mPEG-PLA-tocopherol was previously applied as described above, and the content in the flask was distilled under reduced pressure in a rotary evaporator to remove the solvent. 600 ul of distilled water was added to the flask which was then gently shaken to dissolve the residue, thereby preparing a composition containing siRNA/dimyDETA/mPEG-PLA-tocopherol (5k-4k).

Example 11

Preparation of Composition Containing siRNA/1,4-Dimysteroyl Diethylenetriamine (dimyDETA)/mPEG-PLA-Tocopherol (5k-4k) (Selective Removal of Organic Solvent after Preparation of Double Emulsion)

830 ug of dimyDETA was dissolved in 41.5 ul of chloroform, and 25 ug of siRNA was dissolved in 20 ul of distilled water. 15 mg of mPEG-PLA-tocopherol (5k-4k) was also dissolved in 130 ul of chloroform. Of the solution of 15 mg of mPEG-PLA-tocopherol, a portion corresponding to 3 mg of mPEG-PLA-tocopherol (20 wt %) was placed in a one-neck round bottom flask, 1 ml of chloroform was added and mixed thereto, and then, distilled under reduced pressure in a rotary evaporator to remove the solvent. The dimyDETA solution and the remaining portion of the solution of mPEG-PLA-tocopherol corresponding to 12 mg of mPEG-PLA-tocopherol were mixed with each other, and the aqueous solution of siRNA was added dropwise thereto while the mixture solution was sonicated using a sonicator, thereby preparing an emulsion. The emulsion was added dropwise to 1 ml of distilled water while the solution was sonicated using a sonicator, thereby preparing a double emulsion. The double emulsion was placed in the one-neck round bottom flask to which 3 mg of mPEG-PLA-tocopherol was previously applied as described above, and the content in the flask was distilled under reduced pressure in a rotary evaporator to remove the chloroform, thereby preparing a composition containing siRNA/dimyDETA/mPEG-PLA-tocopherol (5k-4k).

Example 12

Preparation of Composition Containing siRNA/1,8-Dilinoleoyl Tetraethylenepentamine (diliTEPA)/mPEG-PLA-Tocopherol (5k-4k) (Removal of Organic Solvent after Preparation of Emulsion)

367.3 ug of diliTEPA was dissolved in 91.8 ul of chloroform, and 25 ug of siRNA was dissolved in 20 ul of distilled water. 15 mg of mPEG-PLA-tocopherol (5k-4k) was also dissolved in 100 ug of chloroform. Of the solution of 15 mg of mPEG-PLA-tocopherol, a portion corresponding to 3 mg of mPEG-PLA-tocopherol (20 wt %) was placed in a one-neck round bottom flask, 1 ml of chloroform was added and mixed thereto, and then, distilled under reduced pressure in a rotary evaporator to remove the solvent. The diliTEPA solution and the remaining portion of the solution of mPEG-PLA-tocopherol corresponding to 12 mg of mPEG-PLA-tocopherol were mixed with each other, and the aqueous solution of siRNA was added dropwise thereto while the mixture solution was sonicated using a sonicator, thereby preparing an emulsion. The emulsion was placed in the one-neck round bottom flask to which 3 mg of mPEG-PLA-tocopherol was previously applied as described above, and the content in the flask was distilled under reduced pressure in a rotary evaporator to remove the solvent. 600 ul of distilled water was added to the flask which was then gently shaken to dissolve the residue, thereby preparing a composition containing siRNA/diliTEPA/mPEG-PLA-tocopherol (5k-4k).

Example 13

Preparation of Composition Containing siRNA/1,8-Dilinoleoyl Tetraethylenepentamine (diliTEPA)/mPEG-PLA-Tocopherol (5k-4k) (Selective Removal of Organic Solvent after Preparation of Double Emulsion)

367.3 ug of diliTEPA was dissolved in 91.8 ul of chloroform, and 25 ug of siRNA was dissolved in 20 ul of distilled water. 15 mg of mPEG-PLA-tocopherol (5k-4k) was also dissolved in 100 ug of chloroform. Of the solution of 15 mg of mPEG-PLA-tocopherol, a portion corresponding to 3 mg of mPEG-PLA-tocopherol (20 wt %) was placed in a one-neck round bottom flask, 1 ml of chloroform was added and mixed thereto, and then, distilled under reduced pressure in a rotary evaporator to remove the solvent. The diliTEPA solution and the remaining portion of the solution of mPEG-PLA-tocopherol corresponding to 12 mg of mPEG-PLA-tocopherol were mixed with each other, and the aqueous solution of siRNA was added dropwise thereto while the mixture solution was sonicated using a sonicator, thereby preparing an emulsion. The emulsion was added dropwise to 1 ml of distilled water while the solution was sonicated using a sonicator, thereby preparing a double emulsion. The double emulsion was placed in the one-neck round bottom flask to which 3 mg of mPEG-PLA-tocopherol was previously applied as described above, and the content in the flask was distilled under reduced pressure in a rotary evaporator to remove the chloroform, thereby preparing a composition containing siRNA/diliTEPA/mPEG-PLA-tocopherol (5k-4k).

Test Example 4

Comparison of siRNA Content Between Compositions Containing siRNA/mPEG-PLA-tocopherol (5k-4k)/dimyDETA or diliTEPA In order to examine a change in the content of siRNA according to the preparation method, the content of siRNA in each of the compositions prepared in Examples 10, 11, 12 and 13 was measured.

Using a modified Bligh & Dyer extraction method, siRNA in each of the siRNA/cationic lipid-containing amphiphilic block copolymer micelles prepared in Examples 10, 11, 12 and 13 was quantified. Specifically, each of the polymeric micelles was dissolved in a solution of 50 mM sodium phosphate and 75 mM NaCl (pH 7.5), and a Bligh & Dyer single phase was made in the solution, after which the solution was extracted with 100 mM sodium phosphate, 150 mM NaCl (pH 7.5) and chloroform, and siRNA in the aqueous layer was quantified using Ribogreen reagent (Invitrogen).

As a sterile filter, Millipore 0.45 um PVDF filter was used. The results of the test are shown in Table 10 below.

TABLE 10

| | Preparation method | Kind of polymer | Composition ratio | Content after filtration |
|---|---|---|---|---|
| Example 10 | Removal of solvent after preparation of emulsion | siRNA/dimyDETA/mPEG-PLA-tocopherol (5k-4k) | 5-18-3 | 60.0% |
| Example 11 | Removal of solvent after preparation of double emulsion | SiRNA/dimyDETA/mPEG-PLA-tocopherol (5k-4k) | 5-18-3 | 66.2% |
| Example 12 | Removal of solvent after preparation of emulsion | siRNA/diliTEPA/mPEG-PLA-tocopherol (5k-4k) | 5-18-3 | 12.8% |
| Example 13 | Removal of solvent after preparation of double emulsion | siRNA/diliTEPA/mPEG-PLA-tocopherol (5k-4k) | 5-18-3 | 64.1% |

Example 14

Preparation of Composition Containing siRNA/1,6-Dioleoyl Triethylenetetramine (dioTETA)/mPEG-PLA-Tocopherol (5k-4k) (Removal of Solvent after Preparation of Emulsion)

6.98 mg of dioTETA was dissolved in 350 ul of chloroform, and 200 ug of siRNA was dissolved in 160 ul of distilled water. 40 mg of mPEG-PLA-tocopherol (5k-4k) was dissolved in 133 ul of chloroform. Of the solution of 40 mg of mPEG-PLA-tocopherol, a portion corresponding to 8 mg of mPEG-PLA-tocopherol (20 wt %) was placed in a one-neck round bottom flask, 800 ul of chloroform was added and mixed thereto, and then, distilled under reduced pressure in a rotary evaporator to remove the solvent. The dioTETA solution and the remaining portion of the solution of mPEG-PLA-tocopherol corresponding to 32 mg of mPEG-PLA-tocopherol were mixed with each other, 1 ml of chloroform was added thereto, and the aqueous solution of siRNA was added dropwise thereto while the mixture solution was sonicated using a sonicator, thereby preparing an emulsion. The emulsion was placed in the one-neck round bottom flask to which 8 mg of mPEG-PLA-tocopherol was previously applied as described above, and the content in the flask was distilled under reduced pressure in a rotary evaporator to remove the solvent. 2 ml of distilled water was added to the flask which was then gently shaken to dissolve the residue, thereby preparing a composition containing siRNA/dioTETA/mPEG-PLA-tocopherol (5k-4k).

Example 15

Preparation of Composition Containing siRNA/1,6-Dioleoyl Triethylenetetramine (dioTETA)/mPEG-PLA-Tocopherol (5k-4k) (Selective Removal of Solvent after Preparation of Double Emulsion)

6.98 mg of dioTETA was dissolved in 350 ul of chloroform, and 200 ug of siRNA was dissolved in 160 ul of distilled water. 40 mg of mPEG-PLA-tocopherol (5k-4k) was dissolved in 4 ml of distilled water. To the solution of dioTETA, 450 ul of chloroform was added, and then, the aqueous solution of siRNA was added dropwise thereto while the mixture solution was sonicated using a sonicator, thereby preparing an emulsion. The emulsion was added dropwise to the solution of 40 mg of mPEG-PLA-tocopherol in distilled water while the solution was sonicated using a sonicator, thereby preparing a double emulsion. The double emulsion was placed in a one-neck round bottom flask and distilled under reduced pressure in a rotary evaporator to remove the chloroform, thereby preparing a composition containing siRNA/diliTEPA/mPEG-PLA-tocopherol (5k-4k).

Example 16

Preparation of Composition Containing siRNA/1,6-Dioleoyl Triethylenetetramine (dioTETA)/mPEG-PLA-Tocopherol (5k-4k) (Selective Removal of Solvent after Preparation of Double Emulsion)

6.98 mg of dioTETA was dissolved in 350 ul of chloroform, and 200 ug of siRNA was dissolved in 160 ul of distilled water. 8 mg of mPEG-PLA-tocopherol (5k-4k) was dissolved in 3 ml of chloroform, and 32 mg of mPEG-PLA-tocopherol (5k-4k) was dissolved in 4 ml of distilled water (total amount of mPEG-PLA-tocopherol (5k-4k): 40 mg). The solution of 8 mg (20 wt %) of mPEG-PLA-tocopherol in chloroform was placed in a one-neck round bottom flask and distilled under reduced pressure to remove the solvent. To the solution of dioTETA, 450 ul of chloroform was added, and then, the aqueous solution of siRNA was added dropwise thereto while the mixture solution was sonicated using a sonicator, thereby preparing an emulsion. The emulsion was added to the aqueous solution of 32 mg of mPEG-PLA-tocopherol while the solution was sonicated using a sonicator, thereby preparing a double emulsion. The double emulsion was placed in the one-neck round bottom flask to which 8 mg of mPEG-PLA-tocopherol was previously applied as described above, and the content in the flask was distilled under reduced pressure in a rotary evaporator to selectively remove the chloroform, thereby preparing a composition containing siRNA/dioTETA/mPEG-PLA-tocopherol (5k-4k).

Test Example 5

Comparison of siRNA Content Between Compositions Containing siRNA/mPEG-PLA-Tocopherol (5k-4k)/dimyDETA or diliTEPA In order to examine the change in siRNA content according to the preparation method, the content of siRNA in each of the compositions prepared in Examples 14, 15 and 16 was measured.

Using a modified Bligh & Dyer extraction method, siRNA in each of the siRNA/cationic lipid-containing amphiphilic block copolymer micelles prepared in Examples 14, 15 and 16 was quantified. Specifically, each of the polymeric micelles was dissolved in a solution of 50 mM sodium phosphate and 75 mM NaCl (pH 7.5), and a Bligh & Dyer single phase was made in the solution, after which the solution was extracted with 100 mM sodium phosphate, 150 mM NaCl (pH 7.5) and chloroform, and siRNA in the aqueous layer was quantified using Ribogreen reagent (Invitrogen).

As a sterile filter, Millipore 0.45 um PVDF filter was used. The results of the test are shown in Table 11 below.

TABLE 11

| | Preparation method | Kind of polymer | Composition ratio | Content before filtration | Content after filtration |
|---|---|---|---|---|---|
| Example 14 | Removal of solvent after preparation of emulsion | siRNA/dioTETA/ mPEG-PLA-tocopherol (5k-4k) | 5-15-1 | 25.9% | 14.7% |
| Example 15 | Removal of solvent after preparation of double emulsion | siRNA/dioTETA/ mPEG-PLA-tocopherol (5k-4k) | 5-15-1 | 67.1% | 65.0% |
| Example 16 | Removal of solvent after preparation of double emulsion | siRNA/dioTETA/ mPEG-PLA-tocopherol (5k-4k) | 5-15-1 | 67.8% | 65.4% |

Example 17

Preparation of Composition Containing siRNA/1,6-Dioleoyl Triethylenetetramine (dioTETA)/mPEG-PLA-Tocopherol (5k-4k) (Removal of Solvent after Preparation of Emulsion)

872.5 ug of dioTETA was dissolved in 100 ul of chloroform, and 25 ug of siRNA was dissolved in 20 ul of distilled water. 5 mg of mPEG-PLA-tocopherol (5k-4k) was dissolved in 500 ul of chloroform. The solution of 1 mg (20 wt %) of mPEG-PLA-tocopherol in chloroform was placed in a one-neck round bottom flask and distilled under reduced pressure to remove the solvent. The aqueous solution of siRNA was added dropwise to the mixture solution of dioTETA and 4 mg of mPEG-PLA-tocopherol (5k-4k) while the mixture solution was sonicated using a sonicator, thereby preparing an emulsion. The emulsion was added to the one-neck round bottom flask to which 1 mg of mPEG-PLA-tocopherol was previously applied as described above, and the content in the flask was distilled under reduced pressure in a rotary evaporator to remove the sovent, and 600 ul of distilled water was added to the flask which was then gently shaken to dissolve the residue, thereby preparing a composition containing siRNA/dioTETA/mPEG-PLA-tocopherol (5k-4k).

TABLE 12

| | Composition | Composition ratio | siRNA | lipid | Polymer |
|---|---|---|---|---|---|
| Example 17 | siRNA/1,6-dioTETA/mPEG-PLA-tocopherol (5k-4k) | 5-15-1 | 25 ug | 872.5 ug | 5 mg |

Example 18, 19, 20 and 21

Preparation of Composition Containing siRNA/1,6-Dioleoyl Triethylenetetramine (dioTETA)/mPEG-PLA-Tocopherol (5k-4k) (Selective Removal of Solvent after Preparation of Double Emulsion)

872.5 ug of dioTETA was dissolved in 100 ul of chloroform, and 25 ug of siRNA was dissolved in 20 ul of distilled water. 5 mg of mPEG-PLA-tocopherol (5k-4k) was dissolved in 500 ul of distilled water. To the solution of dioTETA, the aqueous solution of siRNA was added dropwise thereto while the mixture solution was sonicated using a sonicator, thereby preparing an emulsion. The emulsion was added to the aqueous solution of 5 mg of mPEG-PLA-tocopherol while the solution was sonicated using a sonicator, thereby preparing a double emulsion. The double emulsion was placed in the one-neck round bottom flask, and the content in the flask was distilled under reduced pressure in a rotary evaporator to selectively remove the chloroform, thereby preparing a composition containing siRNA/dioTETA/mPEG-PLA-tocopherol (5k-4k) (Example 18).

According to a method similar to the method of Example 18, a composition of Example 19, 20 and 21 were prepared. Specifically, 500 ug, 50 ug and 5 ug of mPEG-PLA-tocopherol (5k-4k) were applied to Example 19, 20 and 21, respectively.

TABLE 13

| | Composition | Composition ratio | siRNA | lipid | Polymer |
|---|---|---|---|---|---|
| Example 18 | siRNA/1,6-dioTETA/ mPEG-PLA-tocopherol (5k-4k) | 5-15-1 | 25 ug | 872.5 ug | 5 mg |
| Example 19 | siRNA/1,6-dioTETA/ mPEG-PLA-tocopherol (5k-4k) | 5-15-0.1 | 25 ug | 872.5 ug | 500 ug |
| Example 20 | siRNA/1,6-dioTETA/ mPEG-PLA-tocopherol (5k-4k) | 5-15-0.01 | 25 ug | 872.5 ug | 50 ug |
| Example 21 | siRNA/1,6-dioTETA/ mPEG-PLA-tocopherol (5k-4k) | 5-15-0.001 | 25 ug | 872.5 ug | 5 ug |

Test Example 6

Comparison of siRNA Content Between Compositions Containing siRNA/mPEG-PLA-Tocopherol (5k-4k)/dioTETA In order to examine the change in siRNA content according to the preparation method and the quantity of polymer, the content of siRNA in each of the compositions prepared in Examples 17, 18, 19, 20, and 21 was measured.

Using a modified Bligh & Dyer extraction method, siRNA in each of the siRNA/cationic lipid-containing amphiphilic block copolymer micelles prepared in Examples 17, 18, 19, 20, and 21 was quantified. Specifically, each of the polymeric micelles was dissolved in a solution of 50 mM sodium phosphate and 75 mM NaCl (pH 7.5), and a Bligh & Dyer single phase was made in the solution, after which the solution was extracted with 100 mM sodium phosphate, 150 mM NaCl (pH 7.5) and chloroform, and siRNA in the aqueous layer was quantified using Ribogreen reagent (Invitrogen).

As a sterile filter, Millipore 0.45 urn PVDF filter was used.

The results of the test are shown in Table 14 below.

TABLE 14

| | Preparation method | Kind of polymer | Composition ratio | Content before filtration | Content after filtration |
|---|---|---|---|---|---|
| Example 17 | Removal of solvent after preparation of emulsion | siRNA/ dioTETA/ mPEG-PLA-tocopherol (5k-4k) | 5-15-1 | 33.86% | 22.33% |
| Example 18 | Removal of solvent after preparation of double emulsion | siRNA/ dioTETA/ mPEG-PLA-tocopherol (5k-4k) | 5-15-1 | 89.19% | 85.18% |
| Example 19 | Removal of solvent after preparation of double emulsion | siRNA/ dioTETA/ mPEG-PLA-tocopherol (5k-4k) | 5-15-0.1 | 90.19% | 77.28% |
| Example 20 | Removal of solvent after preparation of double emulsion | siRNA/ dioTETA/ mPEG-PLA-tocopherol (5k-4k) | 5-15-0.01 | 79.00% | 66.06% |
| Example 21 | Removal of solvent after preparation of double emulsion | siRNA/ dioTETA/ mPEG-PLA-tocopherol (5k-4k) | 5-15-0.001 | 94.89% | 81.40% |

Test Example 7

Comparison of Particle Size Between Compositions Containing siRNA/mPEG-PLA-Tocopherol (5k-4k)/dioTETA In order to examine the formation of micelle comprising siRNA, cationic lipid and amphiphilic block copolymer, the particle size and the free siRNA of each of the compositions prepared in Examples 18, 19, 20, and 21 was measured.

Using dynamic light scattering (DLS) method, particle size of each of the siRNA/cationic lipid-containing amphiphilic block copolymer micelles prepared in Examples 18, 19, 20, and 21 was measured. Specifically, He—Ne laser was used as a light source and the DLS instrument was ELS-8000 manufactured by Photal Otsuka Electronics.

Using agarose gel electrophoresis, free siRNA of each of the compositions prepared in Examples 18, 19, 20, and 21 was measured.

TABLE 15

| | Preparation method | Kind of polymer | Composition ratio | Particle size | Free siRNA |
|---|---|---|---|---|---|
| Example 18 | Removal of solvent after preparation of double emulsion | siRNA/ dioTETA/ mPEG-PLA-tocopherol (5k-4k) | 5-15-1 | 95.6 nm | No |
| Example 19 | Removal of solvent after preparation of double emulsion | siRNA/ dioTETA/ mPEG-PLA-tocopherol (5k-4k) | 5-15-0.1 | 89.9 nm | No |
| Example 20 | Removal of solvent after preparation of double emulsion | siRNA/ dioTETA/ mPEG-PLA-tocopherol (5k-4k) | 5-15-0.01 | 96.2 nm | No |
| Example 21 | Removal of solvent after preparation of double emulsion | siRNA/ dioTETA/ mPEG-PLA-tocopherol (5k-4k) | 5-15-0.001 | 101.8 nm | No |

The invention claimed is:

1. A method of preparing a composition for anionic drug delivery, the composition comprising an anionic drug, a cationic lipid and an amphiphilic block copolymer, wherein the anionic drug forms a complex with a cationic lipid, and the complex is entrapped in a micelle structure formed by the amphiphilic block copolymer, the method comprising the steps of:

(1) adding an aqueous solution of the anionic drug to a solution of the cationic lipid in an organic solvent to make an emulsion; and (2) adding an aqueous solvent or an aqueous solution of the amphiphilic block copolymer to form a polymeric micelle, provided that, when the aqueous solvent is added in step (2), the method further comprises either the steps of adding the amphiphilic block copolymer to the solution of the cationic lipid in the organic solvent, which is used in step (1), and removing the organic solvent from the emulsion prepared in step (1), or the steps of removing the organic solvent from the emulsion prepared in step (1), adding thereto a solution of the amphiphilic block copolymer in an organic solvent, and then removing the organic solvent, and when the aqueous solution of the amphiphilic block copolymer is added in step (2), the method further comprises, after step (1) or (2), the step of removing the organic solvent.

2. The method of claim 1, wherein the method comprises the steps of:

(1-i) adding an aqueous solution of the anionic drug to a solution of the cationic lipid in an organic solvent to prepare an emulsion;

(1-ii) removing the organic solvent from the emulsion prepared in step (1-i);

(1-iii) dissolving the amphiphilic block copolymer in an organic solvent, adding the solution to the resultant of step (1-ii) and removing the organic solvent; and (1-iv) adding an aqueous solvent to the resultant of step (1-iii) to form a polymeric micelle.

3. The method of claim 1, wherein the method comprises the steps of:

(2-i) adding an aqueous solution of the anionic drug to a solution of the cationic lipid in an organic solvent to prepare an emulsion;

(2-ii) removing the organic solvent from the emulsion prepared in step (2-i); and (2-iii) mixing an aqueous solution of the amphiphilic block copolymer with the resultant of step (2-ii) to form a polymeric micelle.

4. The method of claim 1, wherein the method comprises the steps of:

(3-i) adding an aqueous solution of the anionic drug to a solution of the cationic lipid and the amphiphilic lipid in an organic solvent to prepare an emulsion;

(3-ii) removing an organic solvent from the emulsion prepared in step (3-i); and (3-iii) adding an aqueous solution to the resultant of step (3-ii), from which the organic solvent was removed, to form a polymeric micelle.

5. The method of claim 1, wherein the method comprises the steps of:

(4-i) adding an aqueous solution of the anionic drug to a solution of the cationic lipid in an organic solvent to prepare an emulsion;

(4-ii) adding the emulsion of (4-i) to an aqueous solution of the amphiphilic block copolymer to prepare a double emulsion; and (4-iii) selectively removing the organic solvent from the double emulsion prepared in step (4-ii), to form a polymeric micelle.

6. The method of claim 1, wherein the method comprises the steps of:

(5-i) adding an aqueous solution of the anionic drug to a solution of the cationic lipid and the amphiphilic block copolymer in an organic solvent to prepare an emulsion;

(5-ii) adding the emulsion of step (5-i) to an aqueous solvent to prepare a double emulsion; and (5-iii) selectively removing the organic solvent from the double emulsion of step (5-ii), to form a polymeric micelle.

7. The method of claim 2, wherein the method further comprises a coating step of dissolving a portion of the amphiphilic block copolymer in an organic solvent, placing the solution of the amphiphilic block copolymer in a vessel and removing the organic solvent from the solution of the amphiphilic block copolymer, thereby coating the inside of the vessel with the amphiphilic block copolymer, wherein the amount of amphiphilic block copolymer that is used in step (1-iii), (2-iii), (3-i), (4-ii) or (5-i) is the unused amount of the amphiphilic block copolymer in the coating step, and step (1-ii), (2-ii), (3-ii), (4-iii) or (5-iii) is carried out in the coated vessel.

8. The method of claim 7, wherein the portion of the amphiphilic block copolymer, which is used in the coating step is 1 to 50 wt % based on the total amount of amphiphilic block copolymer used, and the amount of amphiphilic block copolymer used in step (1-iii), (2-iii), (3-i), (4-ii) or (5-i) is an amount excluding the amount of the portion of the amphiphilic block copolymer, which is used in the coating step.

9. The method of claim 1, wherein the organic solvent which is used to dissolve the cationic lipid or the amphiphilic block copolymer is at least one selected from the group consisting of ethyl acetate, acetonitrile, methylene chloride, chloroform, and dioxane.

10. The method of claim 1, wherein the concentration of the anionic drug in the aqueous solution of the anionic drug is 1 ng/ml to 1 kg/ml, the concentration of the cationic lipid in the solution of the cationic lipid in the organic solvent is 1 pg/ml to 1 kg/ml, and the mixing ratio by volume between the aqueous solution of the anionic drug and the organic solvent solution of the cationic lipid is 1:1-50.

11. The method of claim 1, wherein the anionic drug is a peptide, a protein or a nucleic acid.

12. The method of claim 11, wherein the nucleic acid is at least one selected from the group consisting of RNA, DNA, short interfering RNA (siRNA), an aptamer, antisense oligodeoxynucleotide (ODN), antisense RNA, ribozyme, and DNAzyme.

13. The method of claim 1, wherein the cationic lipid is at least one selected from the group consisting of N,N-dioleyl-N,N-dimethylammonium chloride (DODAC), N,N-distearyl-N,N-dimethylammonium bromide (DDAB), N-(1-(2,3-dioleoyloxy)propyl-N,N,N-trimethylammonium chloride (DOTAP), N,N-dimethyl-(2,3-dioleoyloxy)propylamine (DODMA), 1,2-diacyl-3-trimethylammonium-propane (TAP), 1,2-diacyl-3-dimethylammonium-propane (DAP), 3β-[N—(N',N',N'-trimetylaminoethane)carbomoyl]cholesterol (TC-cholesterol), 3β-[N—(N',N'-dimethylaminoethane)carbamoyl]cholesterol (DC-cholesterol), 3β-[N—(N'-monomethylaminoethane)carbamoyl]cholesterol (MC-cholesterol), 3β-[N-(aminoethane)carbamoyl]cholesterol (AC-cholesterol), cholesteroloxypropane-1-amine (COPA), N—(N'-aminoethane)carbamoylpropanoic tocopherol (AC-tocopherol), and N—(N'-methylaminoethane)carbamoylpropanoic tocopherol (MC-tocopherol).

14. The method of claim 1, wherein the cationic lipid is represented by the following formula 1:

[Formula 1]

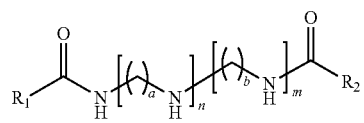

wherein n and m are each 0 to 12, with the proviso that 2≤n+m≤12, a and b are each 1 to 6, and R1 and R2 are each independently selected from saturated and unsaturated hydrocarbon groups having 11 to 25 carbon atoms.

15. The method of claim 14, wherein n and m are independently 1 to 9, with a proviso that 2 n+m 10.

16. The method of claim 15, wherein n and m are 2 to 4 respectively.

17. The method of claim 14, wherein R1 and R2 are each independently selected from the group consisting of lauryl, myristyl, palmityl, stearyl, arachidyl, behenyl, lignoceryl, cerotyl, myristoleyl, palmitoleyl, sapienyl, oleyl, linoleyl, arachidonyl, eicosapentaenyl, erucyl, docosahexaenyl, and cerotyl.

18. The method of claim 1, wherein the amphiphilic block copolymer is an A-B-type block copolymer consisting of a hydrophilic A-block and a hydrophobic B-block.

19. The method of claim 18, wherein the hydrophilic A-block is at least one selected from the group consisting of polyalkyleneglycol, polyvinyl alcohol, polyvinyl pyrrolidone, polyacrylamide, and derivatives thereof, and the hydrophobic B-block is at least one selected from the group consisting of polyester, polyanhydride, polyamino acid, polyorthoester, and polyphosphazine.

* * * * *

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: sense strand of si-Luc, wherein n is T, and two
      Ts are linked by phosphorothioate linkage
<220> FEATURE:
<221> NAME/KEY: misc_feature
```

```
<222> LOCATION: (20)..(21)
<223> OTHER INFORMATION: n is a, c, g, or u

<400> SEQUENCE: 1
cuuacgcuga guacuucgan n                                              21

<210> SEQ ID NO 2
<211> LENGTH: 21
<212> TYPE: RNA
<213> ORGANISM: Artificial Sequence
<220> FEATURE:
<223> OTHER INFORMATION: antisense strand of si-Luc, wherein n is T, and
      two Ts are linked by phosphorothioate linkage
<220> FEATURE:
<221> NAME/KEY: misc_feature
<222> LOCATION: (20)..(21)
<223> OTHER INFORMATION: n is a, c, g, or u

<400> SEQUENCE: 2
ucgaaguacu cagcguaagn n                                              21
```